(12) United States Patent
Semenyuk

(10) Patent No.: US 10,192,026 B2
(45) Date of Patent: Jan. 29, 2019

(54) SYSTEMS AND METHODS FOR GENOMIC PATTERN ANALYSIS

(71) Applicant: Seven Bridges Genomics Inc., Cambridge, MA (US)

(72) Inventor: Vladimir Semenyuk, Pacific Grove, CA (US)

(73) Assignee: Seven Bridges Genomics Inc., Cambridge, MA (US)

( * ) Notice: Subject to any disclaimer, the term of this patent is extended or adjusted under 35 U.S.C. 154(b) by 259 days.

(21) Appl. No.: 15/061,235

(22) Filed: Mar. 4, 2016

(65) Prior Publication Data

US 2016/0259880 A1 Sep. 8, 2016

Related U.S. Application Data

(60) Provisional application No. 62/238,999, filed on Oct. 8, 2015, provisional application No. 62/128,706, filed on Mar. 5, 2015.

(51) Int. Cl.

| | | |
|---|---|---|
| G01N 33/48 | (2006.01) | |
| G01N 33/50 | (2006.01) | |
| G06F 19/16 | (2011.01) | |
| G06F 19/22 | (2011.01) | |

(52) U.S. Cl.
CPC .............. *G06F 19/16* (2013.01); *G06F 19/22* (2013.01)

(58) Field of Classification Search
None
See application file for complete search history.

(56) References Cited

U.S. PATENT DOCUMENTS

| | | |
|---|---|---|
| 5,511,158 A | 4/1996 | Sims |
| 5,583,024 A | 12/1996 | McElroy et al. |
| 5,674,713 A | 10/1997 | McElroy et al. |
| 5,700,673 A | 12/1997 | McElroy et al. |
| 5,701,256 A | 12/1997 | Marr et al. |

(Continued)

FOREIGN PATENT DOCUMENTS

| | | |
|---|---|---|
| WO | 2007/086935 A2 | 8/2007 |
| WO | 2012096579 A3 | 7/2012 |

(Continued)

OTHER PUBLICATIONS

Szalkowski et al. Graph-based modeling of tandem repeats improves global multiple sequence alignment. Nucleic Acids Research. pp. 1-11. (Year: 2013).*

(Continued)

*Primary Examiner* — Russell S Negin
(74) *Attorney, Agent, or Firm* — Kip L. Bodi

(57) ABSTRACT

The invention provides methods for analyzing sequence data in which a large amount and variety of reference data are efficiently modeled as a reference graph, such as a directed acyclic graph (DAG). The method includes determining positions of k-mers within a reference graph that represents a genomic sequence and known variation, storing the positions of each k-mer in a table entry indexed by a hash of that k-mer, and identifying a region within the reference graph that includes a threshold number of the k-mers by reading from the table entries indexed by hashes of substrings of a subject sequence. The subject sequence may subsequently be mapped to the candidate region.

20 Claims, 16 Drawing Sheets

Specification includes a Sequence Listing.

(56) References Cited

U.S. PATENT DOCUMENTS

| | | |
|---|---|---|
| 6,054,278 A | 4/2000 | Dodge et al. |
| 6,210,891 B1 | 4/2001 | Nyren et al. |
| 6,223,128 B1 | 4/2001 | Allex et al. |
| 6,306,597 B1 | 10/2001 | Macevicz |
| 6,818,395 B1 | 11/2004 | Quake et al. |
| 6,828,100 B1 | 12/2004 | Ronaghi |
| 6,833,246 B2 | 12/2004 | Balasubramanian |
| 6,890,763 B2 | 5/2005 | Jackowski et al. |
| 6,911,345 B2 | 6/2005 | Quake et al. |
| 6,925,389 B2 | 8/2005 | Hitt et al. |
| 6,989,100 B2 | 1/2006 | Norton |
| 7,169,560 B2 | 1/2007 | Lapidus et al. |
| 7,232,656 B2 | 6/2007 | Balasubramanian et al. |
| 7,282,337 B1 | 10/2007 | Harris |
| 7,577,554 B2 | 8/2009 | Lystad et al. |
| 7,598,035 B2 | 10/2009 | Macevicz |
| 7,620,800 B2 | 11/2009 | Huppenthal et al. |
| 7,809,509 B2 | 10/2010 | Milosavljevic |
| 7,835,871 B2 | 11/2010 | Kain et al. |
| 7,885,840 B2 | 2/2011 | Sadiq et al. |
| 7,917,302 B2 | 3/2011 | Rognes |
| 7,960,120 B2 | 6/2011 | Rigatti et al. |
| 8,146,099 B2 | 3/2012 | Tkatch et al. |
| 8,209,130 B1 | 6/2012 | Kennedy et al. |
| 8,340,914 B2 | 12/2012 | Gatewood et al. |
| 8,370,079 B2 | 2/2013 | Sorenson et al. |
| 8,639,847 B2 | 1/2014 | Blaszczak et al. |
| 9,063,914 B2 | 6/2015 | Kural et al. |
| 9,092,402 B2 | 7/2015 | Kural et al. |
| 9,116,866 B2 | 8/2015 | Kural |
| 9,817,944 B2 | 11/2017 | Kural |
| 2002/0164629 A1 | 11/2002 | Quake et al. |
| 2004/0023209 A1 | 2/2004 | Jonasson |
| 2005/0089906 A1 | 4/2005 | Furuta et al. |
| 2006/0024681 A1 | 2/2006 | Smith et al. |
| 2006/0195269 A1 | 8/2006 | Yeatman et al. |
| 2006/0292611 A1 | 12/2006 | Berka et al. |
| 2007/0114362 A1 | 5/2007 | Feng et al. |
| 2007/0166707 A1 | 7/2007 | Schadt et al. |
| 2008/0251711 A1 | 10/2008 | Reilly |
| 2008/0294403 A1 | 11/2008 | Zhu et al. |
| 2009/0026082 A1 | 1/2009 | Rothberg et al. |
| 2009/0119313 A1 | 5/2009 | Pearce |
| 2009/0127589 A1 | 5/2009 | Rothberg et al. |
| 2009/0164135 A1* | 6/2009 | Brodzik ............... C12Q 1/6827 702/20 |
| 2009/0191565 A1 | 7/2009 | Lapidus et al. |
| 2009/0300781 A1 | 12/2009 | Bancroft et al. |
| 2010/0010992 A1 | 1/2010 | Morris |
| 2010/0035252 A1 | 2/2010 | Rothberg et al. |
| 2010/0041048 A1 | 2/2010 | Diehl et al. |
| 2010/0137143 A1 | 6/2010 | Rothberg et al. |
| 2010/0169026 A1 | 7/2010 | Sorenson et al. |
| 2010/0188073 A1 | 7/2010 | Rothberg et al. |
| 2010/0197507 A1 | 8/2010 | Rothberg et al. |
| 2010/0240046 A1 | 9/2010 | Palmer et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Carnevali et al. |
| 2011/0009278 A1 | 1/2011 | Kain et al. |
| 2011/0098193 A1 | 4/2011 | Kingsmore et al. |
| 2011/0207135 A1 | 8/2011 | Faham et al. |
| 2012/0030566 A1 | 2/2012 | Victor |
| 2012/0040851 A1 | 2/2012 | Lieberman et al. |
| 2012/0041727 A1 | 2/2012 | Mishra et al. |
| 2012/0045771 A1* | 2/2012 | Beier ............... C12N 15/1006 435/6.14 |
| 2012/0239706 A1 | 9/2012 | Steinfadt |
| 2012/0330566 A1 | 12/2012 | Chaisson |
| 2013/0029879 A1 | 1/2013 | Shetty et al. |
| 2013/0035904 A1 | 2/2013 | Kuhn |
| 2013/0059738 A1 | 3/2013 | Leamon et al. |
| 2013/0059740 A1 | 3/2013 | Drmanac et al. |
| 2013/0073214 A1 | 3/2013 | Hyland et al. |
| 2013/0124100 A1 | 5/2013 | Drmanac et al. |
| 2013/0289099 A1 | 10/2013 | Goff et al. |
| 2013/0311106 A1 | 11/2013 | White et al. |
| 2014/0012866 A1 | 1/2014 | Bowman et al. |
| 2014/0025312 A1 | 1/2014 | Chin et al. |
| 2014/0051588 A9 | 2/2014 | Drmanac et al. |
| 2014/0066317 A1 | 3/2014 | Talasaz |
| 2014/0129201 A1 | 5/2014 | Kennedy et al. |
| 2014/0136120 A1 | 5/2014 | Colwell et al. |
| 2014/0200147 A1 | 7/2014 | Bartha et al. |
| 2014/0278590 A1 | 9/2014 | Abbassi et al. |
| 2014/0280360 A1 | 9/2014 | Webber et al. |
| 2015/0056613 A1 | 2/2015 | Kural |
| 2015/0057946 A1 | 2/2015 | Kural |
| 2015/0094212 A1 | 4/2015 | Gottimukkala et al. |
| 2015/0110754 A1 | 4/2015 | Bai et al. |
| 2015/0112602 A1 | 4/2015 | Kural et al. |
| 2015/0112658 A1 | 4/2015 | Kural et al. |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0227685 A1 | 8/2015 | Kural |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0344970 A1 | 12/2015 | Vogelstein et al. |
| 2015/0347678 A1 | 12/2015 | Kural |
| 2015/0356147 A1 | 12/2015 | Mishra et al. |
| 2016/0259880 A1 | 9/2016 | Semenyuk |
| 2016/0306921 A1 | 10/2016 | Kural |
| 2016/0364523 A1 | 12/2016 | Locke et al. |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0198351 A1 | 7/2017 | Lee et al. |
| 2017/0199959 A1 | 7/2017 | Locke |
| 2017/0199960 A1 | 7/2017 | Ghose et al. |
| 2017/0242958 A1 | 8/2017 | Brown |

FOREIGN PATENT DOCUMENTS

| | | |
|---|---|---|
| WO | 2012098515 A1 | 7/2012 |
| WO | 2012/142531 A2 | 10/2012 |
| WO | 2015027050 A1 | 2/2015 |
| WO | 2015048753 A1 | 4/2015 |
| WO | 2015058093 A1 | 4/2015 |
| WO | 2015058095 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 2016141294 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Lam et al. Compressed indexing and local alignment of DNA. Bioinformatics, vol. 24, pp. 791-797. (Year: 2008).*

Denoeud et al. Identification of polymorphic tandem repeats by direct comparison of genome sequence from different bacterial strains: a web-based resource. BMC Bioinformatics, vol. 5, article 4, 12 pages. (Year: 2004).*

Berlin, 2014, Assembling large genomes with single-molecule sequencing and locality sensitive hashing, bioRxiv preprint (35 pages); retrieved from the internet on Jan. 29, 2015, at <http://biorxiv.org/content/biorxiv/early/2014/08/14/008003.full.pdf>.

Buhler, 2001, Search algorithms for biosequences using random projection, dissertation, University of Washington (203 pages);

(56) References Cited

OTHER PUBLICATIONS retreived from the internet on Jun. 3, 2016, at <http://www.mathcs.emory.edu/~cheung/papers/Matching/Search-Alg-for-Biosequences-Thesis.pdf>.
Flicek, 2009, Sense from sequence reads: methods for alignment and assembly, Nat Meth Suppl 6(11s):s6-s12.
International Search Report and Written Opinion dated May 5, 2016, for International Patent Application No. PCT/US2016/020899, wiht International Filing Date Mar. 4, 2016 (12 pages).
Lee, 2014, MOSAIK: A hash-based algorithm for accurate next-generation sequencing short-read mapping, PLoS One 9(3):e90581.
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the internet on Jun. 3, 2016, at <http://Lcs.hku.hk/~nikos/seqjoin.pdf>.
Misra, 2011, Anatomy of a hash-based long read sequence mapping algorithm for next generation DNA sequencing, Bioinformatics 27(2):189-195.
Ning, 2001, SSAHA: A fast search method for large DNA databases, Genome Research 11:1725-1729.
Sun, 2006, Pairwise Comparison Between Genomic Sequences and Optical maps, dissertation, New York University (131 pages); retreived from the internet on Jun. 3, 2016, at <https://cs.nyu.edu/mishra/PEOPLE/sun_bing.pdf>.
Thomas, 2014, Community-wide effort aims to better represent variation in human reference genome, Genome Web (11 pages).
Boyer & Moore, 1977, A Fast String Searching Algorithm, Comm ACM 20(10):762-772.
Horspool, 1980, Practical Fast Searching in Strings, Software—Practice & Experience 10:501-506.
Tarhio & Ukkonen, 1993, Approximate Boyer-Moore String Matching, SIAM J Comput 22(2):243-260.
Altschul et al., Optimal Sequence Alignment Using Affine Gap Costs, Bulletin of Mathematical Biology vol. 48, No. 5/6, pp. 603-616, 1986.
Black, 2005, A simple answer for a splicing conundrum, PNAS 102:4927-8.
Carrington et al., 1985, Polypeptide ligation occurs during post-translational modification of concanavalin A, Nature 313:64-67.
Chin et al., 2013, Nonhybrid, finished microbial genome assemblies from long-read SMRTS sequencing data Nature Methods 10(6):563-571.
Compeauet et al., How to apply de Bruijn graphs to genome assembly, Nature Biotechnology vol. 29 No. 11, pp. 987-991.
Dudley and Butte, A quick guide for developing effective bioinformatics programming skills, PLoS Comput Biol 5(12): e1000589 (2009).
Farrar et al., Striped Smith-Waterman speeds database searches six times over other SIMD implementations, vol. 23 No. 2 2007, pp. 156-161.
Florea et al., Gene and alternative splicing annotation with AIR, Genome Res. 2005 15: 54-66.
Goto et al., 2010, BioRuby: bioinformatics software for the Ruby programming language, Bioinformatics 26(20):2617-9.
Gotoh et al., An Improved Algorithm for Matching Biological Sequences, J. Mol. Bid. (1982) 162, 705-708.
Hein et al., A New Method That Simultaneously Aligns and Reconstructs Ancestral Sequences for Any Number of Homologous Sequences, When the Phylogeny is Given. Mol. Biol. E vol. 6(6):649-668. 1989.
Hein et al., A Tree Reconstruction Method That is Economical in the Number of Pairwise Comparisons Used, Mol. Biol. Evol. 6(6):649-668. 1989.
Holland et al., 2008, BioJava: an open-source framework for bioinformatics, Bioinformatics 24(18):2096-97.
Huang, Chapter 3: Bio-Sequence Comparison and Alignment, ser. Curr Top Comp Mol Biol. Cambridge, Mass: The MIT Press, 2002.
International HapMap Consortium, 2005, A haplotype map of the human genome. Nature 437:1299-1320.

LaFramboise, 2009, Single nucleotide polymorphism arrays: a decade of biological, computational and technological advance, Nucleic Acids Res 37(13):4181-4193.
Larkin et al., 2007, Clustal W and Clustal X version 2.0, Bioinformatics 23(21):2947-2948.
Lee and Wang, 2005, Bioinformatics analysis of alternative splicing, Brief Bioinf 6(1):23-33.
Lee, et al., 2002, Multiples sequence alignment using partial order graphs, Bioinformatics 18(3): 452-464.
LeGault and Dewey, 2013, Inference of alternative splicing from RNA-Seq data with probabilistic splice graphs, Bioinformatics 29(18):2300-2310.
Leipzig, et al., 2004, The alternative splicing gallery (ASG): Bridging the gap between genome and transcriptome, Nucl Ac Res 23(13):3977-2983.
Lipman and Pearson, 1985, Rapid and sensitive protein similarity searches, Science 227(4693):1435-41.
Ma et al., Multiple genome alignment based on longest path in directed acyclic graphs. Int. J. Bioinformatics Research and Applications, vol. 6, No. 4, 2010, abstract only.
Manolio, et al., 2010, Genome wide association studies and assessment of the risk of disease, NEJM 363(2):166-76.
Margulies et al., 2005, Genome sequencing in micro-fabricated high-density picotiter reactors, Nature, 437:376-380.
Miller et al., 2010, Assembly Algorithms for Next-Generation Sequencing Data, Genomics 95(6): 315-327.
Mount et al., Multiple Sequence Alignment, Bioinformatics, 2001, Cold Spring Harbor Laboratory Press, Cold Spring Harbor, New York, pp. 139-204.
Nagalakshmi et al., RNA-Seq: A Method for Comprehensive Transcriptome Analysis, Current Protocols in Molecular Biology 4.11.1.13, Jan. 2010, 13 pages.
Needleman & Wunsch, 1970, A general method applicable to the search for similarities in the amino acid sequence of two proteins, J Mol Biol, 48(3):443-453.
Oshlack et al., From RNA-seq reads to differential expression results. Genoome Bio 2010, 11:220, pp. 1-10.
Pe'er., et al, 2006, Evaluating and improving power in whole-genome association studies using fixed marker sets. Nat. Genet., 38, 663-667.
Potter et al., ASC: An Associative-Computing Paradigm, Computer , 27(11):19-25, 1994.
Quail, et al., 2012, A tale of three next generation sequencing platforms: comparison of Ion Torrent, Pacific Biosciences and Illumina MiSeq sequencers, BMC Genomics 13:341.
Rognes et al., Faster Smith-Waterman database searches with inter-sequence SIMD parallelisation,Bioinfomiatics 2011, 12:221.
Rognes et al., ParAlign: a parallel sequence alignment algorithm for rapid and sensitive database searches, Nucleic Acids Research, 2001, vol. 29, No. 7 1647-1652.
Rognes et al., Six-fold speed-up of Smith-Waterman sequence database searching using parallel processing on common microprocessors, Bioinformatics vol. 16 No. 8 2000, pp. 699-706.
Rothberg, et al., 2011, An integrated semiconductor device enabling non-optical genome sequencing, Nature 475:348-352.
Saebo et al., PARALIGN: rapid and sensitive sequence similarity searches powered by parallel computing technology, Nucleic Acids Research, 2005, vol. 33, Web Server issue W535-W539.
Sievers et al., 2011, Fast, scalable generation of high-quality protein multiple sequence alignments using Clustal Omeag, Mol Syst Biol 7:539.
Slater & Birney, 2005, Automated generation of heuristics for biological sequence comparison, BMC Bioinformatics 6:31.
Smith & Waterman, 1981, Identification of common molecular subsequences, J Mol Biol, 147(1):195-197.
Smith et al., Multiple insert size paired-end sequencing for deconvolution of complex transcriptions, RNA Bio 9:5, 596-609; May 2012.
Smith et al., Identification of Common Molecular Subsequences, J. Mol. Biol. (1981) 147, 195-197.
Soni and Meller, 2007, Progress toward ultrafast DNA sequencing using solid-state nanopores, Clin Chem 53 (11):1996-2001.
Stephens, et al,. 2001, A new statistical method for haplotype reconstruction from population data, Am J Hum Genet 68:978-989.

(56) References Cited

OTHER PUBLICATIONS

Wang, et al., 2011, Next generation sequencing has lower sequence coverage and poorer SNP-detection capability in the regulatory regions, Scientific Reports 1:55.
Waterman, et al., 1976, Some biological sequence metrics, Adv. in Math. 20(3):367-387.
Wellcome Trust Case Control Consortium, 2007, Genome-wide association study of 14,000 cases of seven common diseases and 3,000 shared controls, Nature 447:661-678.
Wu et al., Fast and SNP-tolerant detection of complex variants and splicing in short reads, Bioinformatics, vol. 26 No. 7 2010, pp. 873-881.
Yu et al., The construction of a tetraploid cotton genome wide comprehensive reference map, Genomics 95 (2010) 230-240.
Bertone et al., 2004, Global identification of human transcribed sequences with genome tiling arrays, Science 306:2242-2246.
Chang et al., 2005, The application of alternative splicing graphs in quantitative analysis of alternative splicing form from EST database, Int J. Comp. Appl. Tech 22(1): 14.
Delcher et al., 1999, Alignment of whole genomes, Nucleic Acids Research, 27(11):2369-2376.
Garber et al., 2011, Computational methods for transcriptome annotation and quantification using RNA-Seq, Nat Meth 8(6):469-477.
Harrow et al., 2012, GENCODE: The reference human genome annotation for The ENCODE Project, Genome Res 22:1760-1774.
Heber et al., 2002, Splicing graphs and EST assembly problems, Bioinformatics 18 Suppl:181-188.
Kim et al., 2005, ECgene: Genome-based EST clustering and gene modeling for alternative splicing, Genome Research 15:566-576.
Kurtz et al., 2004, Versatile and open software for comparing large genomes, Genome Biology, 5:R12.
Langmead et al., 2009, Ultrafast and memory-efficient alignment of short DNA sequences to the human genome, Genome Biology 10:R25.
Li et al., 2008, SOAP: short oligonucleotide alignment program, Bioinformatics 24(5):713-14.
Li et al., 2009, SOAP2: an improved ultrafast tool for short read alignment, Bioinformatics 25(15): 1966-67.
Lindgreen, 2012, AdapterRemoval: easy cleaning of next-generation sequence reads, BMC Res Notes 5:337.
Nakao et al., 2005, Large-scale analysis of human alternative protein isoforms: pattern classification and correlation with subcellular localization signals, Nucl Ac Res 33(8):2355-2363.
Pearson et al., 1988, Improved tools for biological sequence comparison, PNAS 85(8):2444-8.
Shao et al., 2006, Bioinformatic analysis of exon repetition, exon scrambling and trans-splicing in humans, Bioinformatics 22:692-698.
Wang et al., 2009, RNA-Seq: a revolutionary tool for transcriptomics, Nat Rev Genet 10(I):57-63.
Xing et al., 2006, An expectation-maximization algorithm for probabilistic reconstructions of full-length isoforms from splice graphs, Nucleic Acids Research, 34:3150-3160.
Grabherr et al., 2011, Full-length transcriptome assembly from RNA-Seq data without a reference genome, Nature Biotechnology 29(7):644-654.
Costa et al., 2010, Uncovering the Complexity of Transcriptomes with RNA-Seq, Journal of Biomedicine and Biotechnology Article ID 853916:1-19.
LeGault et al., 2010, Learning Probalistic Splice Graphs from RNA-Seq data, pages.cs.wisc.edu/~legault/cs760_writeup.pdf; retrieved from the internet on Apr. 6, 2014.
Trapnell et al., 2010, Transcript assembly and quantification by RNA-Seq reveals unannotated trancripts and isoform switching during cell differentiation, Nature Biotechnology 28(5):511-515.
Guttman et al., 2010, Ab initio reconstruction of cell type-specific transcriptomes in mouse reveals the conserved multi-exonic structure of lincRNAs, Nature Biotechnology 28(5):503-510.
NIH Public Access Author Manuscript, Trapnell et al., 2010, Transcript assembly and abundance estimation from RNA-Seq reveals thousands of new transcripts and swtiching among isoforms, NIH-PA Author Manuscript.
NIH Public Access Author Manuscript, Guttman et al., 2010, Ab initio reconstruction of transcriptomes of pluripotent and lineage committed cells reveals gene structures of thousands of lincRNAs, NIH-PA Author Manuscript.
Kent, 2002, BLAT—The Blast-Like Alignment Tool, Genome Research 4:656-664.
Lam et al., 2008, Compressed indexing and local alignment of DNA, Bioinformatics 24(6):791-97.
Yu, et al., A tool for creating and parallelizing bioinformatics pipelines, DOD High Performance Computing Conf., 417-420 (2007).
Hoon et al., 2003, Biopipe: A flexible framework for protocol-based bioinformatics analysis, Genome Research 13(8)1904-1915.
Altera, 2007, Implementation of the Smith-Waterman algorithm on reconfigurable supercomputing platform, White Paper ver 1.0 (18 pages).
Fitch, 1970, Distinguishing homologous from analogous proteins, Systematic Zoology 19:99-113.
Haas et al., 2004, DAGchainer: a tool for mining segmental genome duplications and synteny, Bioinformatics 20(18):3643-3646.
Lee, 2003, Generating consensus sequences from partial order multiple sequence alignment graphs, Bioinformatics 19(8):999-1008.
Li, et al., 2009, The Sequence Alignment/Map format and SAMtools, Bioinformatics 25(16):2078-9.
Mardis, 2010, The $1,000 genome, the $100,000 analysis?, Genome Med 2:84-85.
Nagarajan & Pop, 2013, Sequence assembly demystified, Nat Rev 14:157-167.
Raphael, 2004, A novel method for multiple alignment of sequences with repeated and shuffled elements, Genome Res 14:2336-2346.
Rodelsperger, 2008, Syntenator: Multiple gene order alignments with a gene-specific scoring function, Alg Mol Biol 3:14.
Schwikowski & Vingron, 2002, Weighted sequence graphs: boosting iterated dynamic programming using locally suboptimal solutions, Disc Appl Mat 127:95-117.
Stewart, et al., 2011, A comprehensive map of mobile element insertion polymorphisms in humans, PLoS Genetics 7(8):1-19.
Yanovsky, et al., 2008, Read mapping algorithms for single molecule sequencing data, Procs of the 8th Int Workshop on Algorithms in Bioinformatics 5251:38-49.
Durham, et al., EGene: a configurable pipeline system for automated sequence analysis, Bioinformatics 21(12):2812-2813 (2005).
Danecek et al., 2011, The variant call format and VCFtools, Bionformatics 27(15):2156-2158.
Li et al., 2010, A survey of sequence alignment algorithms for next-generation sequencing, Briefings in Bionformatics 11(5):473-483.
Schneeberger et al., 2009, Sumaltaneous alignment of short reads against multiple genomes, Genome Biology 10(9):R98.2-R98.12.
International Search Report and Written Opinion dated Dec. 11, 2014, for International Patent Application No. PCT/US14/52065, filed Aug. 21, 2014, (18 pages).
International Search Report and Written Opinion dated Jan. 27, 2015, for International Patent Application No. PCT/US2014/060680, filed Oct. 215, 2014, (11 pages).
International Search Report and Written Opinion dated May 11, 2015, for International Patent Application No. PCT/US2015/015375 with International Filing Date Feb. 11, 2015 (12 pages).
Bao et al., 2013, BRANCH: boosting RNA-Seq assemblies with partial or related genomic sequences, Bioinformatics.
Bertrand et al., 2009, Genetic map refinement using a comparative genomic approach, J Comp Biol 16(10):1475-1486.
International Preliminary Report on Patentability issued in application No. PCT/US2014/052065 dated Feb. 23, 2016.
Haas et al. "DAGchainer: a tool for mining segmental genome duplications and synteny", Bioinformatics, vol. 20, pp. 3643-3646 (2004).

(56) References Cited

OTHER PUBLICATIONS

Agarwal, 2013, SINNET: Social Interaction Network Extractor from Text, Proc IJCNLP 33-36.
Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13): i352-i360.
Airoldi, 2008, Mixed membership stochastic blockmodels, JMLR 9:1981-2014.
Alioto et al., A comprehensive assessment of somatic mutation detection in cancer using whole-genome sequencing, Nature Communications, Dec. 9, 2015.
Bansal, 2008, An MCMC algorithm for haplotype assembly from whole-genome sequence data, Genome Res 18:1336-1346.
Barbieri, 2013, Exome sequencing identifies recurrent SPOP, FOXA1 and MED12 mutations in prostate cancer, Nature Genetics 44:6 685-689.
Beerenwinkel, 2007, Conjunctive Bayesian Networks, Bernoulli 13(4), 893-909.
Browning et al, Haplotype phasing: existing methods and new developments, 2011, vol. 12, Nature Reviews Genetics.
Caboche et al, Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Chuang, 2001, Gene recognition based on DAG shortest paths, Bioinformatics 17(Suppl. 1):s56-s64.
Craig, 1990, Ordering of cosmid clones covering the Herpes simplex virus type I (HSV-I) genome: a test case for fingerprinting by hybridisation, Nucleic Acids Research 18:9 pp. 2653-2660.
Denoeud, 2004, Identification of polymorphic tandem repeats by direct comparison of genome sequence from different bacterial strains: a web-based resource, BMC Bioinformatics 5:4 pp. 1-12.
DePristo, 2011, A framework for variation discovery and genotyping using next-generation DNA sequencing data, Nat Gen 43:491-498.
Durbin, 2014, Efficient haplotype matching and storage using the positional Burrows-Wheeler transform (PBWT), Bioinformatics 30(9):1266-1272.
Endelman, 2011, New algorithm improves fine structure of the barley consensus SNP map, BMC Genomics 12(1):407 (and whole document).
Exam Report issued in EP14803268.3.
Examination Report issued in SG 11201601124Y.
Extended European Search Report issued in EP 14837955.5.
Extended European Search Report issued in EP 14847490.1.
Extended European Search Report issued in EP 14854801.9.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
Gotoh, 1999, Multiple sequence alignment: algorithms and applications, Adv Biophys 36:159-206.
Grasso, 2004, Combining partial order alignment and progressive multiple sequence alignment increases alignment speed and scalability to very large alignment problems, Bioinformatics 20(10):1546-1556.
He, 2010, Optimal algorithms for haplotype assembly from whole-genome sequence data, Bioinformatics 26:i183-i190.
Homer, 2010, Improved variant discovery through local re-alignment of short-read next generation sequencing data using SRMA, Genome Biol 11(10):R99.
Hutchinson, 2014, Allele-specific methylation occurs at genetic variants associated with complex diseases, PLoS One 9(6):e98464.
International Search Report and Written Opinion dated Aug. 31, 2017, for International Application No. PCT/US2017/018830 with International Filing Date Feb. 22, 2017, (11 pages).
International Search Report and Written Opinion dated Mar. 31, 2015 for International Application No. PCT/US2015/010604 filed Jan. 8, 2015 (13 pages).
International Search Report and Written Opinion dated Apr. 19, 2017 for International Patent Application No. PCT/US2017/012015, (14 Pages).
International Search Report and Written Opinion dated Feb. 17, 2015, for International Patent Application No. PCT/US2014/061156, filed Oct. 17, 2014 (19 pages).
International Search Report and Written Opinion dated Jan. 10, 2017, for International Patent Application No. PCT/US16/57324 with International Filing Date Oct. 17, 2016, (7 pages).
International Search Report and Written Opinion dated Mar. 19, 2015, for International Application No. PCT/US2014/061162 with International Filing Date Oct. 17, 2014, (12 pages).
International Search Report and Written Opinion dated Apr. 7, 2017, for International Patent Application No. PCT/US17/13329, filed Jan. 13, 2017, (9 pages).
International Search Report and Written Opinion dated Dec. 30, 2014, for International Patent Application No. PCT/US14/58328, filed Sep. 30, 2014, (22 pages).
International Search Report and Written Opinion dated Feb. 4, 2015, for International Patent Application No. PCT/US2014/061198, filed Oct. 17, 2014, (8 pages).
International Search Report and Written Opinion dated Feb. 10, 2015, for International Patent Application No. PCT/US2014/060690, filed Oct. 15, 2014, (11 pages).
International Search Report and Written Opinion dated Feb. 4, 2015, for Patent Application No. PCT/US2014/061158, filed Oct. 17, 2014, (11 pages).
International Search Report and Written Opinion dated Sep. 2, 2016, for International Patent Application No. PCT/US2016/033201 with International Filing Date May 19, 2016, (14 pages).
International Search Report and Written Opinion dated Sep. 7, 2016, for International Application No. PCT/US2016/036873 with International filing date Jun. 10, 2016, (8 pages).
Kano, 2010, Text mining meets workflow: linking U-Compare with Taverna, Bioinformatics 26(19):2486-7.
Kehr, 2014, Genome alignment with graph data structures: a comparison, BMC Bioinformatics 15:99.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Koolen, 2008, Clinical and Molecular Delineation of the 17q21.31 Microdeletion Syndrome, J Med Gen 45(11):710-720.
Kumar, 2010, Comparing de novo assemblers for 454 transcriptome data, BMC Genomics 11:571.
Lecca, 2015, Defining order and timing of mutations during cancer progression: the TO-DAG probabilistic graphical model, Frontiers in Genetics, vol. 6 Article 309 1-17.
Lee, 2014, Accurate read mapping using a graph-based human pan-genome, ASHG 2014 Abstracts.
Li, 2009, Fast and accurate short read alignment with Burrows-Wheeler Transform. Bioinformatics 25:1754-60.
Lucking, 2011, PICS-Ord: unlimited coding of ambiguous regions by pairwise identity and cost scores ordination, BMC Bioinf 12:10.
Lupski, 2005, Genomic disorders: Molecular mechanisms for rearrangements and conveyed phenotypes, PLoS Genetics 1(6):e49.
Mazrouee, 2014, FastHap: fast and accurate single individual haplotype reconstructions using fuzzy conflict graphs, Bioinformatics 30:i371-i378.
McSherry, 2001, Spectral partitioning of random graphs, Proc 42nd IEEE Symp Found Comp Sci 529-537.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.

(56) References Cited

OTHER PUBLICATIONS

Newman, 2013, Community detection and graph portioning, Europhys Lett 103(2):28003, arXiv:1305.4974v1.

Parks, 2015, Detecting non-allelic homologous recombination from high-throughput sequencing data, Genome Biol 16:17.

Peixoto, 2014, Efficient Monte Carlo and greedy heuristic for the inference of stochastic block models, Phys. Rev. E 89, 012804.

Pruesse, 2012, SINA: Accurate high-throughput multiple sequence alignment of ribosomal RNA genes, Bioinformatics 28:14 1823-1829.

Rajaram, 2013, Pearl millet [*Pennisetum glaucum* (L.) R. Br.] consensus linkage map constructed using four RIL mapping populations and newly developed EST-SSRs, BMC Genomics 14(1):159.

Robertson, 2010, De novo assembly and analysis of RNA-seq data, Nat Meth 7(11):909.

Ronquist, 2012, MrBayes 3.2: efficient Bayesian phylogenetic inference and model choice across a large model space, Syst Biol 61(3):539-42.

Sato, 2008, Directed acyclic graph kernels for structural RNA analysis, BMC (BioMed Central) Bioinformatics 9(318).

Sosa, 2012, Next-Generation Sequencing of Human Mitochondrial Reference Genomes Uncovers High Heteroplasmy Frequency, PLoS One 8(10):e1002737.

Sturgeon, RCDA: a highly sensitive and specific alternatively spliced transcript assembly tool featuring upstream consecutive exon structures, Genomics, Dec. 2012, 100(6): 357-362.

Subramanian, 2008, DIALIGN-TX: greedy and progessive approaches for segment-based multiple sequence alignment, Alg Mol Biol 3(1):1-11.

Sudmant, 2015, An integrated map of structural variation in 2,504 human genomes, Nature 526:75-81.

Szalkowski, 2012, Fast and robust multiple sequence alignment with phylogeny-aware gap placement, BMC (BioMed Central) Bioinformatics 13(129).

Trapnell, 2009, TopHat: discovering splice junctions with RNA-Seq, Bioinformatics 25:1105-1111.

Uchiyama et al., CGAT: a comparative genome analysis tool for visualizing alignments in the analysis of complex evolutionary changes between closely related genomes, 2006, e-pages 1-17, vol. 7:472; BMC Bioinformatics.

Wang, 2009, RNA-Seq: a revolutionary tool for transcriptomics, Nat Rev Genet 10(1):57-63.

Written Opinion issued in SG 11201601124Y.

Written Opinion issued in SG 11201603044S.

Yang, 2013, Leveraging reads that span multiple single nucleotide polymorphisms for haplotype inference from sequencing data, Bioinformatics 29(18):2245-2252.

Zeng, 2013, PyroHMMvar: a sensitive and accurate method to call short indels and SNPs for Ion Torrent and 454 data, Bioinformatics 29:22 2859-2868.

* cited by examiner

5'-CCCAGAACGTTGCATCGTAGACGAGTTTCAGC-3'
(SEQ ID NO. 1) Published reference genome & allele 1

5'-CCCAGAACGTTGCTATGCAACAAGGGACATCGTAGACGAGTTTCAGC-3'
(SEQ ID NO 2) allele 2

5'-CCCAGAACGTTGCTATGCAGGAAGGGACATCGTAGACGAGTTTCAGC-3'
(SEQ ID NO 3) allele 3

5'-TTGCTATGCAGGAAGGGACATCG-3'
(SEQ ID NO 4) Sequence read

5'-CCCAGAACGTTG-3'
(SEQ ID NO 5) Node 1

5'-CATCGTAGACGAGTTTCAGCATT-3'
(SEQ ID NO 6) Node 2

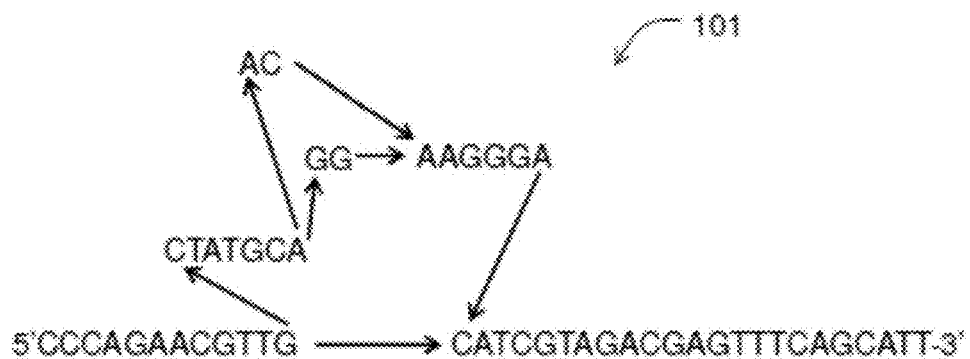

FIG. 1

101 all-seqs.fasta

>1
CCCAGAACGTTG

>2
CATCGTAGACGAGTTTCAGCATT

>3
CTATGCA

>4
AAGGGA

>5
AC

>6
GG all-seqs-DAG.txt

GACATGAGATTCCACATGATTCTGATT (SEQ ID NO: 7)
GACATGAGATTCCAATTCTGATT (SEQ ID NO: 8)
GACATGAGAGTCCACATGATTCTGATT (SEQ ID NO: 9)
GACATGAGAGTCCAATTCTGATT (SEQ ID NO: 10)

```
Identified Data String for Path 1:

GACATGAGAGTCCAATTCTGATT (SEQ ID NO: 7)

Blocks (S=2, B=3):

GAC (1)
   CAT (2)
      TGA (3)
         AGA (4)
            AGT (5)
               TCC (6)
                  CAA (7)
                     ATT (8)
                        TCT (9)
                           TGA (10)
                              ATT (11)
```

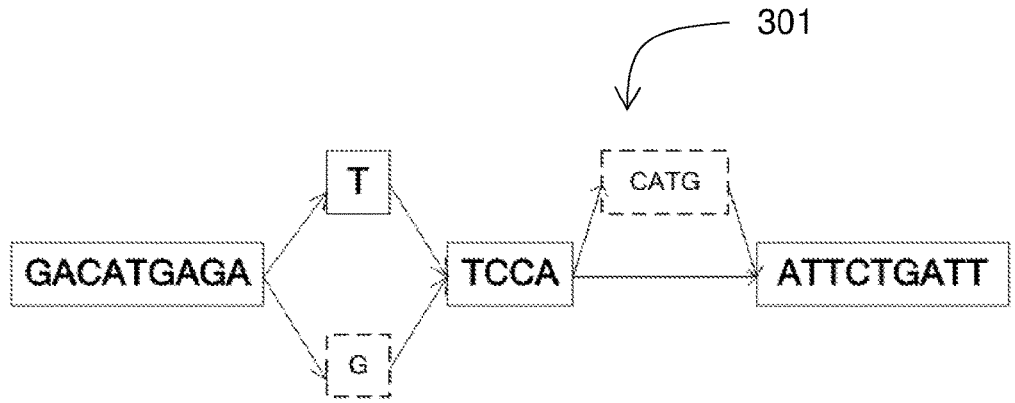
Identified Data String for Path 2:
GACATGAGATTCCAATTCTGATT (SEQ ID NO: 8)
Blocks (S=2, B=3):
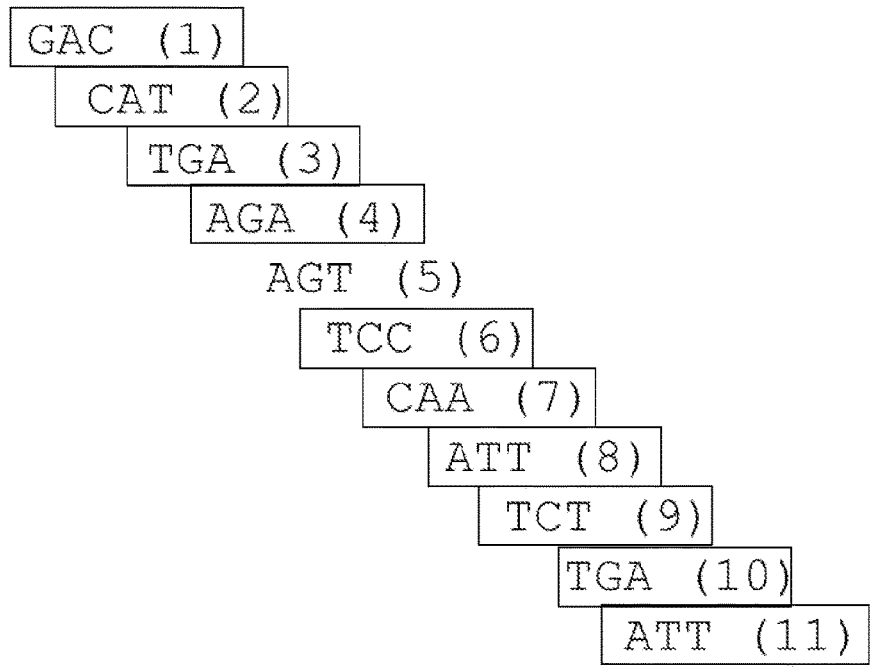
FIG. 5

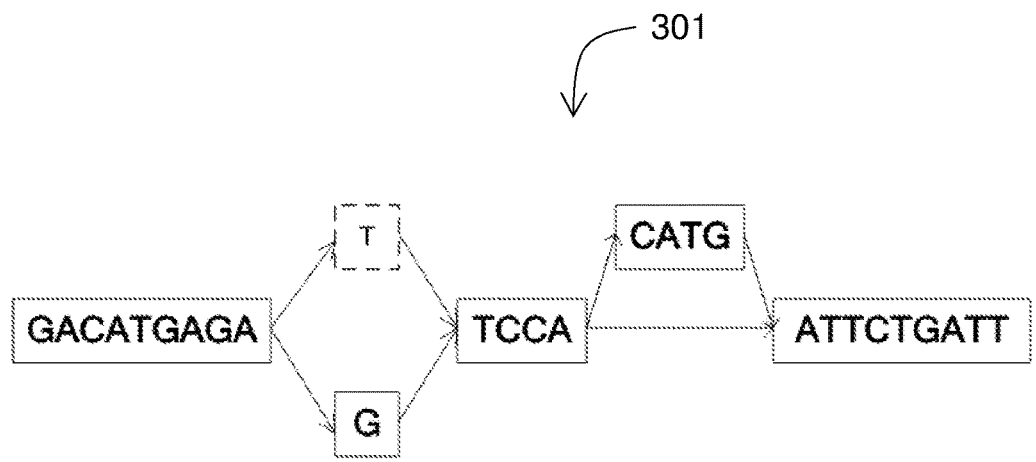
Identified Data String for Path 3:
GACATGAGAGTCCACATGATTCTGATT (SEQ ID NO: 9)
Blocks (S=2, B=3):
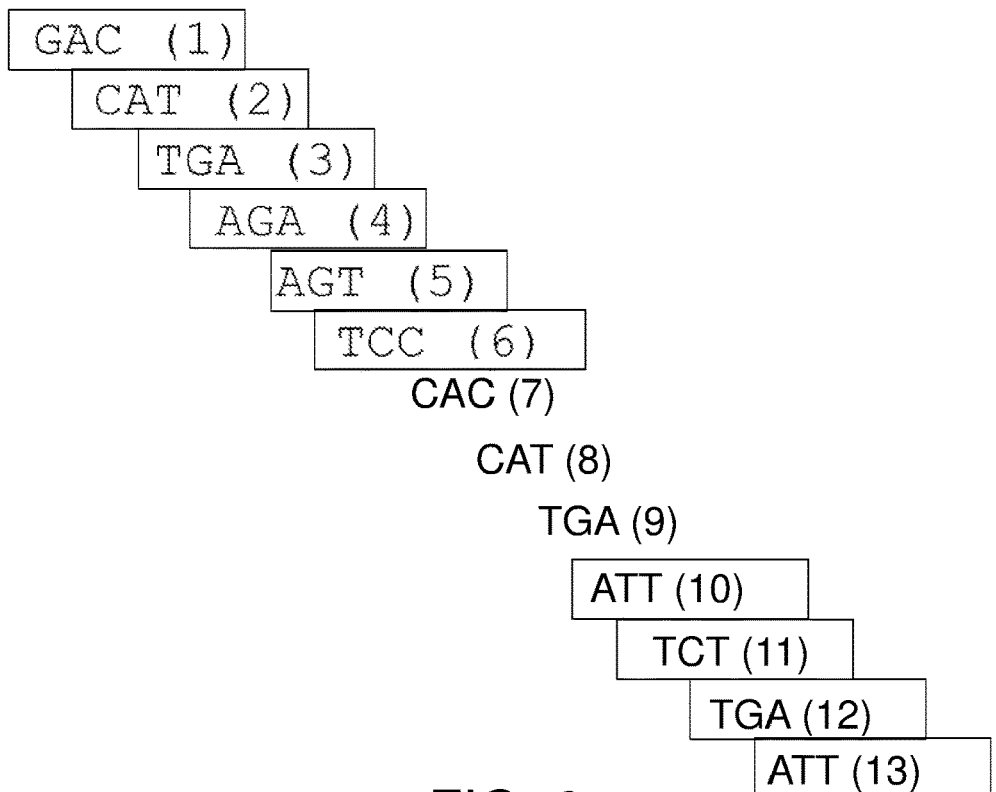
FIG. 6

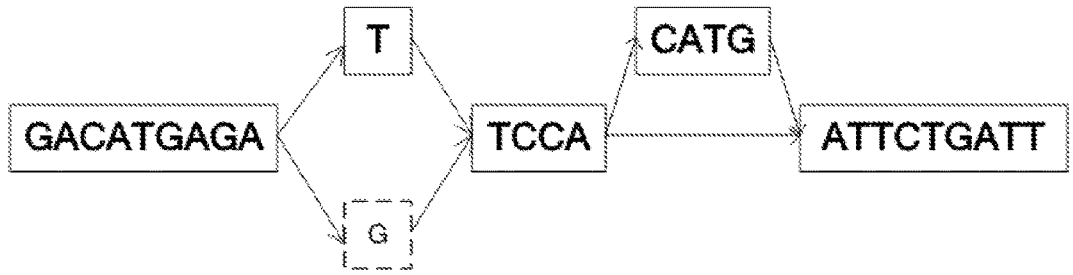
Identified Data String for Path 4:
GACATGAGATTCCACATGATTCTGATT (SEQ ID NO: 10)
Blocks (S=2, B=3):
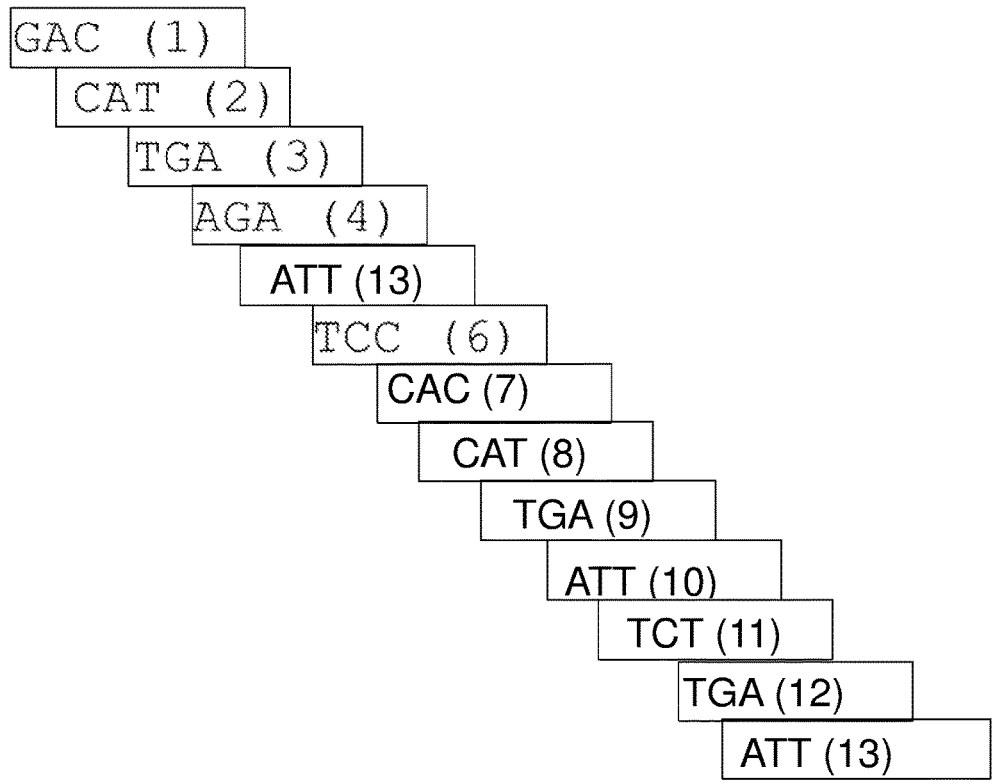
FIG. 7

```
Pattern String: ACATGA

B = 3

Blocks: ACA, CAT, ATG, TGA

Hash(ACA) not in search index for DAG 301

Hash(ATG) not in search index for DAG 301

Hash(CAT) present in search index for DAG 301

Hash(TGA) present in search index for DAG 301
```

TTGGATATGGG (SEQ ID NO. 11)    ATCGAA (read)
TTGGATCGAATTATGGG (SEQ ID NO. 12)
    AT    CGAA (read)
TTGGAT →CGAATT →ATGGG (SEQ ID NO. 12)
TTGGAT ─────────────→ ATGGG (SEQ ID NO. 11)
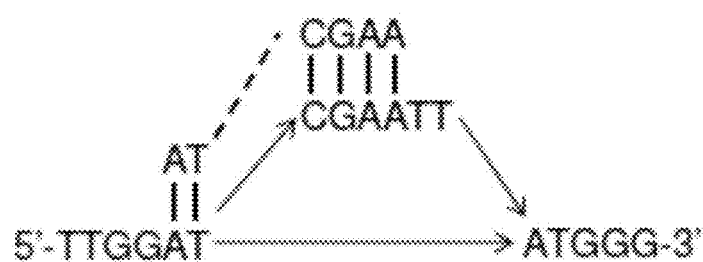
FIG. 15

FIG. 16 ns and Methods for Analyzing Genetic Information", filed Mar. 5, 2015, and U.S. Provisional Patent Application Ser. No. 62/238,999 for "Systems and Methods for Genomic Pattern Analysis," filed Oct. 8, 2015, the disclosures of which are incorporated by reference.

SEQUENCE LISTING

This application contains a sequence listing which has been submitted in ASCII format via EFS-Web and is hereby incorporated by reference in its entirety. The ASCII-formatted sequence listing, created on Mar. 4, 2016, is named SBG-015-01US-Sequences_ST25.txt, and is 2,410 bytes in size.

FIELD OF THE INVENTION

The invention relates to analyzing genetic information.

BACKGROUND

A person's genetic information has the potential to reveal much about their health and life. A risk of cancer or a genetic disease may be revealed by the sequences of the person's genes, as well the possibility that his or her children could inherit a genetic disorder. Genetic information can also be used to identify an unknown organism, such as potentially infectious agents discovered in samples from public food or water supplies. Next-generation sequencing (NGS) technologies are available that can sequence entire genomes quickly. Sequencing by NGS produces a very large number of short sequence reads. Each sequence read represents a short sequence of part of the genome of an organism. Unfortunately, analyzing short sequences is not an easy task.

Some approaches to analyzing sequence reads involve mapping the sequence reads to a reference genome. Mapping reads to a reference can be done by aligning each read to a relevant portion of the reference. The amount and nature of reference genome data presents significant obstacles to successfully mapping sequence reads. Not only have many complete genomes been sequenced, even if the sequence reads are from a known species, there may be a great amount of known genetic variation in that species, i.e., a great diversity of different genotypes among members of the species. For example, the 1,000 Genomes Project is seeking to sequence the genomes of 1,000 humans. It quickly becomes computationally intractable to perform an exhaustive alignment for even a single sequence read against the entire length of each and every one of the known human genomes. In fact, it is not even a trivial problem to simply store and represent all of the complete sequences of all of the known genomes for some organisms. Thus whether screening a patient for a genetic disease or probing an unknown sample for a pathogen, existing analytical approaches are not up to the task of making all of the relevant comparisons that should be made to confidently analyze sequence reads. Unfortunately, sometimes where additional information is known, existing methods do not fully exploit that information for read mapping. For example, for a pair of paired-end reads, existing methods compare the location for each match of a mate against the location of each match for the other mate. Thus even where the first set of matches are analyzed with respect to distance between elements of a pair is $O(n^2)$ in the number of candidates identified in the first filtering stage. Analysis that require resources on the order of $O(n^2)$ pose a significant challenge and may be infeasible or cost-prohibitive.

SUMMARY

In certain aspects, the invention provides a method for analyzing a genetic sequence. The method includes determining positions of k-mers within a reference graph (such as a directed acyclic graph, or "DAG") that represents a genomic sequence and known variation in the genomic sequence, storing the positions of each k-mer in a table entry indexed by a hash of that k-mer, and identifying regions within the reference graph that include a threshold number of the k-mers as found in a query by reading from the table entries indexed by hashes of substrings of query. The query may be a sequence read or paired-end sequence read. Segments of the query are mapped to the regions within the reference graph. The regions within the reference graph may be identified as candidate mapping regions and the mapping may include aligning the segments of the query to the candidate mapping regions. Preferably, the query includes genetic sequences obtained from an organism and the mapping step further includes describing a mutation in the organism. In certain embodiments, the query includes genetic sequences from a patient and the mapping step comprises identifying a mutation in the patient's genome. The method may include providing a report that includes information identifying the patient and information about a condition associated with the mutation such as a hereditary disorder.

In preferred embodiments, the reference graph comprises a plurality of node and edge objects that each stores a list of objects that it is adjacent to. Each node and edge object may store a list of one or more adjacent objects. Mapping a query can comprise finding an optimal alignment between the query and the identified candidate mapping region. Finding an optimal alignment may include finding a highest-scoring trace through a multi-dimensional matrix. Preferably, finding the highest-scoring trace comprises using a computer system to calculate match scores between the reads and at least some of the node and edge objects in the reference graph, and looking backwards to predecessor objects in the graph to identify a back-trace with an optimal score. Each list may include pointers to physical locations in memory of the adjacent objects. Preferably, at least one path through the graph gives a substantially entire sequence of at least one human chromosome.

In preferred embodiments, the reference graph is a genomic reference graph, a structure in which a genomic sequence is represented as a base branch or path, and known variations from the genomic sequence are represented as divergent branches or paths from the base path. Objects corresponding to the genomic sequence and known variations are connected to one other via other objects that define a structure conducive to implementation via adjacency lists or other spatial addressing of computer memory. The described structure for implementing a reference genome graph is compact with very fast lookups. The reference graph can represent a very large number of variations in a genome and methods of the invention can be used to quickly identify parts of one or a few of those variations of interest in a particular application, to which a sequence read should be aligned.

To identify the candidate alignment region, many small sections of a certain fixed size of k symbols, or "k-mers," of the reference graph can be put into a computer hash function. The hash function calculates an index as a function of the k-mer. The index identifies an entry in a hash table, and the positions of the k-mer within the reference graph are stored in that entry, i.e., in the entry indexed by the hash of the k-mer. In other words, the entry contains positions of all k-mers that have this index. A pattern sequence, such as a sequence read, is analyzed by hashing some or all of its k-mers and the corresponding entries of the reference graph hash table are accessed to read positions within the reference graph where those sequence read k-mers can be found. Sections of the reference graph where a threshold number of k-mer positions are found are identified as candidate regions within the represented genomes for alignment or mapping of the sequence read. By the described implementation, a sequence read can be mapped to a "good fit" position within a very large number of reference genomes very rapidly. With the candidate "good fit" position identified, a pairwise alignment or other analytical operations such as mutation or variant calling may be performed. Since hashing allows one to locate a given value rapidly—e.g., without iterating over all the entries in an array—a sequence read can be mapped to a reference very fast. Since a reference graph can store a great amount of genetic variation, a sequence read can be mapped to an appropriate portion very quickly. Since sequence reads can be mapped to biologically relevant reference sequences very quickly, a patient's genetic information can be discerned, or genetic sequences can be identified quickly even against a background of all genetic variety represented in the system.

In certain aspects, the invention provides a method for analyzing a genetic sequence. The method includes determining positions of k-mers within a reference graph that represents a reference genome and known variation, storing the positions of each k-mer in a table entry indexed by a hash of that k-mer, and identifying a region within the graph that includes a threshold number of the k-mers by reading from the table entries indexed by hashes of substrings of a subject sequence. The subject sequence may then be mapped to the region within the reference graph. The region within the reference graph may be used to identify a "candidate region" for mapping the subject sequence. Typically the identified region will include a number of different regions on different branches of, or paths through, the reference graph, all defined by a range of location identifiers.

The method can include populating the hash table for use as a search index. In some embodiments, populating the hash table includes tracing each path through the reference graph and, for every S-th position of a path, calculating a hash index for a block of genomic data symbols of a fixed size B (i.e., a k-mer, where B=k) that starts at that position. A location identifier (such as a number, starting at 0, that increments up by 1 for each position being added to the hash table) is added to the entry for the calculated hash index. In some embodiments, location identifiers are numbered independently for each path, so the identifiers are not unique among different paths. Remembering that the reference graph is implemented as a graph in which some objects (e.g., edges) store known genetic sequences, different paths may contain the same graph objects. To avoid indexing the same data multiple times, positions of blocks entirely located inside edges that have already been indexed as parts of other paths may be excluded from indexing. In some embodiments, a genomic reference graph will be large enough such that each index will point to multiple corresponding location identifiers (i.e., each table entry will include a plurality of positions). Any collisions may be resolved according to known hash function techniques for collision resolution.

Searching the search index for candidate regions for local alignment may include creating a "search list" of hash indexes from the hash table discussed above for each read. In some embodiments, a search list of hash lists is created for each read by calculating a hash index for each block of B base pairs in the read.

A search procedure is employed which looks for regions inside the graph which are similar to the read in size and which contain a substantial number of block matches with the read. An efficient search would leverage the strict order of location identifiers inside hash lists. In some embodiments, an initial set of positions to be considered is identified by taking the first (lowest-value) location identifier from each hash list in the search list. The highest-value location identifier within the set is identified. If the number of location identifiers in the set within a "look-back" interval L of that highest-value location identifier is greater than a threshold T, the range within or near the interval is a "candidate" for where the read might align; if not, it is discarded. The next set to be considered is created by replacing one of the identifiers with the next-in-order identifier belonging to the same hash list (i.e., hash list that contains the identifier being replaced); this next-in-order identifier is always the smallest identifier among all possible next-in-order identifiers (these are determined by picking one next-in-order candidate from each hash list if such identifier exists). The steps are repeated until the set consists of the highest-value location identifiers in each relevant hash list (i.e., there are no more location identifiers to be added).

In a preferred embodiment, a 4-index is calculated for each block of B base pairs in the sequence read. In order to be able to find reversed matches and matches belonging to the complementary strand, for each block position inside the read 4 different hash index values are calculated: a hash index for the original block, the reversed block (i.e., the block with the order of the base pairs reversed), the complementary block (for DNA: A replaced with T, C replaced with G and vice versa; for RNA: A replaced with U, C replaced with G and vice versa), and the reverse-complementary block. This means for each block position 4 different search indexes are calculated and, thus, 4 search lists are added to consideration. As a result, with a 4-index the total number of positions identifiers being analyzed increases by 4 times. With a 4-index, the increase in complexity is compensated for by a significant improvement in ability to detect and identify not just simple genome variations like SNPs, but also insertions, deletions or translocations. It becomes possible to detect some non-trivial types of variations like inversions or transposons. However, in other embodiments, only a 2-index is calculated for each block of B base pairs, including the original and reverse complement strands, as these are the most likely sequences to be encountered when using most next-generation sequencing technologies.

Candidate regions may be reported along with the number of location identifiers within the threshold and whether they resulted from matches to "original", inverted, complementary, or reverse-complementary blocks (if a-4 index is used). What type of blocks have been matched is important because certain combinations of block types are more biologically plausible than others. Optionally, candidates can be reported ranked according to a score based on number of blocks matched and different weights for different types of blocks and combinations.

Methods of the invention can be used in a variety of analytical contexts. In some embodiments, the subject sequence is a sequence read from a nucleic acid sequencing instrument. The mapping step may include aligning the subject sequence to the region within the reference graph, which may include aligning to a candidate mapping region. In certain embodiments, the subject sequence is a genetic sequence obtained from an organism and the mapping step further includes describing a mutation in the organism. The subject sequence may be a genetic sequence from the patient and the mapping step may include identifying a mutation in the patient's genome. The method may include providing a report that includes information identifying the patient and information about a condition such as a hereditary disorder associated with the mutation.

The reference graph may be implemented as a structure that includes a plurality of node and edge objects that each stores a list of objects adjacent to that object, such that variations in the genome are represented as paths through the reference graph. Each node and edge object may store a list of one or more adjacent objects. Embodiments of the invention can use spatial addressing. For example, where adjacency lists are used, each list may include pointers to physical locations in memory of the adjacent objects. Once one or more candidate regions has been identified, mapping the subject sequence may include finding an optimal alignment between the subject sequence and the identified region by finding a highest-scoring trace through a multi-dimensional matrix. Finding the highest-scoring trace may be done by using a computer system to calculate match scores between the reads and at least some of the node and edge objects in the reference graph, and looking backwards to predecessor objects in the reference graph to identify a back-trace with an optimal score. Finding an optimal alignment may include finding a highest-scoring trace through the reference graph by: calculating match scores between the subject sequences and at least some of the node and edge objects in the reference graph, and dereferencing at least some of the pointers to read predecessor objects in the reference graph from their referenced locations in memory, wherein a path through predecessor objects with a maximal sum of match scores is the highest-scoring trace through the reference graph.

Aspects of the invention provide a method for analyzing a genetic sequence by representing a plurality of known genomic sequences in a tangible storage medium as a reference graph in which substrings of the genomic sequences are stored in edge objects that are connected to one another via vertex objects. For each of a plurality of k-mers in the reference graph, the method includes listing that k-mer's positions within the graph in an entry in a hash table wherein that entry is indexed by a hash of that k-mer, obtaining a subject sequence from a subject organism, and determining positions within the graph of k-mers in the subject sequence by reading hash table entries indexed by hashes of the k-mers in the subject sequence. A portion of the reference graph is identified in which a threshold number of subject k-mers appears as a candidate target within the plurality of known genomic sequences for alignment of the subject sequence.

In some embodiments, identifying the portion of the reference graph in which the threshold number of subject k-mers appears as the candidate target includes determining that at least the threshold number of subject k-mers appears within a predetermined distance of one another.

In certain aspects, the invention provides a system for analyzing a genetic sequence. The system includes a processor coupled to a memory and is operable to determine positions of k-mers within a reference graph, store the positions of each k-mer in a table entry indexed by a hash of that k-mer, and identify a region within the reference graph that includes a threshold number of the k-mers by reading from the table entries indexed by hashes of substrings of a subject sequence. The system maps the subject sequence to the candidate mapping region.

The system can populate the hash table for use as a search index by tracing each path through the reference graph and, for every S-th position of a path, calculating a hash index for a block of genomic data symbols of a fixed size B (i.e., a k-mer, where B=k) that starts at that position. A location identifier (a number, starting at 0, that increments up by 1 for each position being added to the hash table) is added to the hash list for the calculated hash index.

The system may search the search index for candidate mapping regions for local alignment by creating a "search list" of hash lists for each subject sequence. In some embodiments, a "search list" of hash lists is created for each read by calculating a hash index for each block of B base pairs in the read and taking the set of hash lists from the hash table corresponding to the calculated indices. In some embodiments, the system identifies an initial set of positions to be considered by taking the first (lowest-value) location identifier from each hash list in the search list. The highest-value location identifier within the set is identified. If the number of location identifiers in the set within a "look-back" interval L of that highest-value location identifier is greater than a threshold T, the range within the interval is a "candidate" for where the read might align; if not, it is discarded. The next set to be considered may be created by replacing one of the identifiers with the next-in-order identifier belonging to the same hash list (i.e., hash list that contains the identifier being replaced); this next-in-order identifier is always the smallest identifier among all possible next-in-order identifiers (these are determined by picking one next-in-order candidate from each hash list if such identifier exists). The steps are repeated until the set consists of the highest-value location identifiers in each relevant hash list (i.e., there are no more location identifiers to be added). The system may calculate and use a 4-index or 2-index as discussed above.

The system may report candidate mapping regions along with the number of location identifiers within the threshold.

In some embodiments, the subject sequence is a sequence read from a nucleic acid sequencing instrument. The system may map the read by performing an alignment. The system may call mutations or be used to identify unknown organisms. In certain embodiments, the subject sequence is a genetic sequence from the patient and the mapping step comprises identifying a mutation in the patient's genome and the system provides a report that includes information identifying the patient and information about a condition such as a hereditary disorder associated with the mutation.

The system may store the reference graph in non-transitory memory using a plurality of node and edge objects that each stores a list of objects that it is adjacent to. Each node and edge object can store a list of one or more adjacent objects. In some embodiments, each list includes pointers to physical locations in memory of the adjacent objects. Once one or more candidate regions has been identified, the system can align the subject sequence to the identified region, e.g., by finding a highest-scoring trace through a multi-dimensional matrix. In certain embodiments, finding the highest-scoring trace comprises using the system to calculate match scores between the reads and at least some of the node and edge objects in the reference graph, and looking backwards to predecessor objects in the reference graph to identify a back-trace with an optimal score. More particularly, the system may find an optimal alignment by finding a highest-scoring trace through the reference graph by a process that includes calculating match scores between the subject sequences and at least some of the node and edge objects in the reference graph and dereferencing at least some of the pointers to read predecessor objects in the reference graph from their referenced locations in memory, wherein a path through predecessor objects with a maximal sum of match scores is the highest-scoring trace through the reference graph.

Related aspects of the invention provide a computer system for analyzing a genetic sequence. The system stores a plurality of known genomic sequences in a tangible storage medium connected to a processor as a reference graph in which substrings of the genomic sequences are stored in edge objects that are connected to one another via vertex objects. For each of a plurality of k-mers in the reference graph, the processor lists that k-mer's positions within the reference graph in an entry in a hash table wherein that entry is indexed by a hash of that k-mer. The system can be used to obtain a subject sequence from a subject organism, determine positions within the DAG of k-mers in the subject sequence by reading hash table entries indexed by hashes of the k-mers in the subject sequence, and identify a portion of the DAG in which a threshold number of subject k-mers appears as a candidate target within the plurality of known genomic sequences for alignment of the subject sequence. Identifying the portion of the DAG in which the threshold number of subject k-mers appears as the candidate target may be done by determining that at least the threshold number of subject k-mers appears within a predetermined distance of one another.

Where the subject sequence is a sequence read obtained by sequencing a genome of a patient, the system may align the subject sequence to the portion of the reference graph to determine genetic information about the subject sequence. Where the subject sequence is a genetic sequence from the patient, the system may be used to identify a mutation in the patient's genome and provide a report that includes information identifying the patient and information about a condition associated with the mutation.

Where the subject sequence is a sequence read obtained by sequencing an unknown nucleic acid from a sample, the system may align the sequence read to the portion of the reference graph, identify an organism associated with one of the plurality of known genomic sequences that contains the portion, and identify the organism as the source of the unknown nucleic acid.

The invention provides a method for analyzing sequence data using a reference graph even where the sequence data has structure other than being a single contiguous sequence read, such as in the case of paired-end reads where two non-contiguous reads are known to have a certain orientation and placement on a genome. Systems and methods of the invention efficiently map a query sequence to a target even where the query has a non-contiguous structure, the target is a directed acyclic graph, or both. In certain embodiments, methods of the invention treat the query (e.g., a set of two or more sequences separated by gaps) as a single unit to be aligned to the target. The invention uses a "sliding window" (or "look-back interval") approach, treating the two or more sequences as a single input. This obviates additional stages of comparing proto-alignments for all combinations of segments so that the mapping operation does not require an $O(n^2)$ step and immediately finds candidate regions. The invention includes exemplary ways to treat the non-contiguous structure. In some embodiments, the component sequences are joined into a contiguous query by 'wildcard' characters that are considered to match any character in the target and the contiguous query is mapped to the target by, e.g., alignment techniques.

One example of a query with non-contiguous structure is a pair of paired-end reads. Methods of the invention treats the entire paired-end item (two reads with a gap between them) as a single unit to be aligned. The invention uses a "sliding window" (or "look-back interval") approach, treating both reads as a single input. In applying the sliding-window/look-back search technique to the paired-end problem, the reference sequence is scanned for suitable complex matches, i.e., matches in which the "seed" searched for includes more than just symbols to be matched and symbols representing a gap between the mates.

There are several kinds of ways to implement the invention for mapping a pair of paired-end reads to a genomic reference graph. In some embodiments, the two mates are joined with 'wildcard' characters that are considered to match any base pair and then align the filled-in read. Both the sliding-window/lookback approach and other standard alignment methods (e.g., any method based on Smith-Waterman or a related algorithm) could then be applied straightforwardly.

In certain embodiments, the location identifiers of k-mers from the 5' sequence read and 3' sequence read of a pair of paired-end sequence reads are determined by reading hash table entries indexed according to hashes a read k-mers. A global ordering of location identifiers for the 5' and 3' sequence reads is then created, and locations in the global ordering in which both the 5' and 3' sequence reads have a substantial number of block matches within a window are identified as candidate mapping regions.

In another embodiment, a method for analyzing a genetic sequence comprises obtaining a reference graph representing a genomic sequence and known variation in the genomic sequence, in which substrings of the genomic sequence and known variation are stored in objects connected to one another to form a plurality of paths through the graph. The method continues by identifying a data string from each path of the plurality of paths through the graph, each data string representing a concatenation of the substrings of genomic sequence and known variation in the genomic sequence stored in objects through the path. For each data string, a plurality of k-mers in the path are identified, and each identified k-mer's location within the graph is listed in an entry in a search index, wherein that entry is indexed according to a hash of that k-mer and contains the locations of all k-mers having that index. Candidate mapping locations within the reference graph for a query sequence are found by identifying a plurality of query k-mers from the query sequence, determining the locations of at least one query k-mer within the graph by reading search index entries indexed according to hashes of query k-mers, and identifying portions of the graph in which the number of potential matches with different query k-mers is equal to or exceeds a threshold number as candidate targets within the graph for alignment of segments of the query sequence. In certain embodiments, at least one path through the graph gives a substantially entire sequence of at least one human chromosome. In certain embodiments, the query sequence is from a subject organism.

Identifying a plurality of query k-mers from the query sequence can further comprise identifying a plurality of query k-mers for the reverse complement of the query sequence. Each entry of the search index can comprise an ordered list of locations for that indexed k-mer. Each k-mer can comprise a sequence of symbols with fixed length k. In certain embodiments, the fixed length k is within the interval [8,14]. Listing each k-mer's location within the graph can further comprise excluding locations identified in a previous path. The locations can comprise floating point projections for alternate branches. Substrings may be stored in edge objects connected to one another by vertex objects to form a plurality of paths through the graph. Methods can further comprise identifying a best-fit location of the query sequence to the graph by performing a local alignment of the query sequence to each candidate target. In certain embodiments, performing a local alignment comprises using a multi-dimensional Smith-Waterman algorithm. The query sequence may be a non-contiguous query. In certain embodiments, a non-contiguous query comprises a pair of paired-end sequence reads, wherein each sequence read is a paired-end sequence read comprising a 5' sequence read and a 3' sequence read. In these embodiments, the method can further comprise identifying portions of the graph in which the number of potential matches with different query k-mers is equal to or exceeds a threshold number within a window of ordered locations. In certain embodiments, the size of the window is less than 1000 base pairs.

In certain embodiments, identifying a plurality of query k-mers from the sequence read comprises identifying a plurality of query k-mers from the 5' sequence read and the 3' sequence read. In these embodiments, identifying portions of the reference graph in which the number of potential matches with different query k-mers is equal to or exceeds a threshold number as candidate targets can comprise creating a global ordering of locations corresponding to query k-mers from the 5' sequence read and the 3' sequence read, and identifying locations in the global ordering in which both the 5' sequence read and 3' sequence read have query k-mers within a window.

BRIEF DESCRIPTION OF THE DRAWINGS

FIG. 1 illustrates the use of a genomic directed acyclic graph (DAG).

FIG. 2 presents an alternative format of the DAG of FIG. 1.

FIG. 5 shows a second path of four, with a corresponding second data string and plurality of blocks.

FIG. 6 shows a third path of four, with a corresponding third data string and plurality of blocks.

FIG. 7 shows a fourth path of four, with a corresponding fourth data string and plurality of blocks.

FIG. 15 illustrates mapping a sequence read to a reference graph.

FIG. 16 shows matrices representing a sequence comparison.

DETAILED DESCRIPTION

Figure 3:
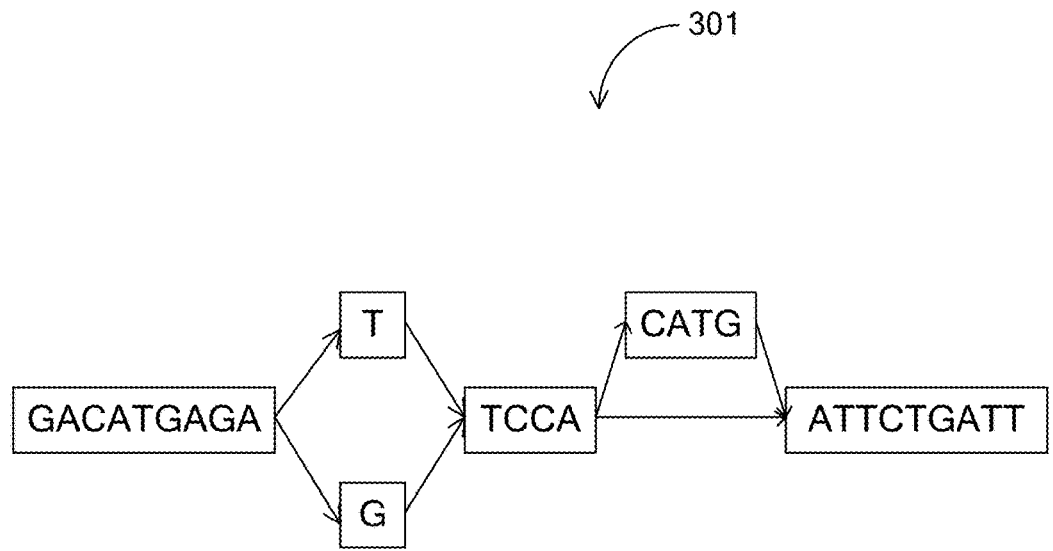
FIG. 3 shows a DAG with several paths.

The invention provides sequence analysis systems and methods that can be used to map a subject sequence, such as a sequence read (e.g., from NGS output) to a reference graph that represents a biological object or set of biological objects, such as a reference genome and known variation in the reference genome. Methods of the invention can very quickly find a region within the graph that is a good candidate region to which the subject sequence should be mapped. Methods of the invention may be used to quickly find, from among numerous references, a portion or portions of a reference that are presumptively homologous to or closely related to (or both) a subject sequence such as an NGS sequence read. Described in greater detail herein, these candidate regions can be identified by determining positions of k-mers within a reference graph, storing the positions of each k-mer in a table entry indexed by a hash of that k-mer, and identifying a region within the graph that a number of k-mers greater than or equal to a certain threshold by reading from the table entries indexed by hashes of substrings of a subject sequence.

Graph Data Structures

Aspects of the invention relate to the use of a reference graph, such as a directed acyclic graph (DAG), that includes sequences from one or more known references. A DAG is understood in the art to refer to data that can be presented as a graph, as well as to a graph that presents that data. The invention provides methods for operating on a DAG that has been stored as data that can be read by a computer system for bioinformatics processing or for presentation as a graph. The DAG can represent a genomic sequence (such as a human chromosome) and known variation in the genomic sequence, in which substrings of the genomic sequence and known variation are stored in objects (such as node objects and edge objects) connected to one another to form a plurality of paths through the DAG. A DAG can be saved in any suitable format including, for example, a list of nodes and edges, a matrix or a table representing a matrix, in a language built with syntax for graphs, in a general markup language purposed for a graph, or others.

In some embodiments, a DAG is stored as a list of nodes and edges. One such way is to create a text file that includes all nodes, with an ID assigned to each node, and all edges, each with the node ID of starting and ending node. Thus, for example, were a DAG to be created for two sentences, "See Jane run," and "Run, Jane run,", a case-insensitive text file could be created. Any suitable format could be used. For example, the text file could include comma-separated values. Naming this DAG "Jane" for future reference, in this format, the DAG "Jane" may read as follows: 1 see, 2 run, 3 jane, 4 run, 1-3, 2-3, 3-4. One of skill in the art will appreciate that this structure is easily applicable to genomic sequences, and the accompanying discussion below.

In certain embodiments, a DAG is stored as a table representing a matrix (or an array of arrays or similar variable structure representing a matrix) in which the (i, j) entry in the N×N matrix denotes that node i and node j are connected (where N is a vector containing the nodes in genomic order). For the DAG to be acyclic simply requires that all non-zero entries be above the diagonal (assuming nodes are represented in genomic order). In a binary case, a 0 entry represents that no edge is exists from node i to node j, and a 1 entry represents an edge from i to j. One of skill in the art will appreciate that a matrix structure allows values other than 0 to 1 to be associated with an edge. For example, any entry may be a numerical value indicating a weight, or a number of times used, reflecting some natural quality of observed data in the world. A matrix can be written to a text file as a table or a linear series of rows (e.g., row 1 first, followed by a separator, etc.), thus providing a simple serialization structure.

One useful way to serialize a matrix DAG would be to use comma-separated values for the entries, after defining the nodes. Using this format, the DAG "Jane" would include the same node definitions as for above, followed by matrix entries. This format could read as:

1 see, 2 run, 3 jane, 4 run
,,1,\,,1,\,,,1\,,,
where entries of zero (0) are simply omitted and '\' is a newline character.

Embodiments of the invention include storing a DAG in a language built with syntax for graphs. For example, The DOT Language provided with the graph visualization software packages known as Graphviz provides a data structure that can be used to store a DAG with auxiliary information and that can be converted into graphic file formats using a number of tools available from the Graphviz web site. Graphviz is open source graph visualization software. Graph visualization is a way of representing structural information as diagrams of abstract graphs and networks. It has applications in networking, bioinformatics, software engineering, database and web design, machine learning, and in visual interfaces for other technical domains. The Graphviz layout programs take descriptions of graphs in a simple text language, and make diagrams in useful formats, such as images and scalable vector graphics for web pages; PDF or Postscript for inclusion in other documents; or display in an interactive graph browser.

In related embodiments, a DAG is stored in a general markup language purposed for a graph. Following the descriptions of a linear text file, or a comma-separated matrix, above, one of skill in the art will recognize that a language such as XML can be used (extended) to create labels (markup) defining nodes and their headers or IDs, edges, weights, etc. However a DAG is structured and stored, embodiments of the invention involve using nodes to represent genomic sequences with edges connecting the nodes to create paths through the DAG that represent genome-scale genomic sequences.

In a preferred embodiment, a library is developed that provides core elements of genome graph representation as well as manipulation routines. For example, library elements can be developed in a language that provides for low-level memory manipulation such as C++ and compiled to provide binary elements. A genomic DAG may be represented as a set of edge and vertex objects linked to each other.

To represent the graph, adjacency lists may be used wherein vertices and edges are stored as physical objects. A vertex or edge stores lists of edges/vertices that it is adjacent to. In certain embodiments, nucleotide sequences and metadata are stored in edge objects. The usage of adjacency lists simplifies local graph traversal. Adjacency lists prove to be a very efficient way to represent a genomic DAG. The genomic-scale reference DAG, when implemented using computer-executable instructions, can effectively leverage specifics of hardware memory addressing for creating efficient adjacency lists. For example, the implementation of a genomic-scale genomic reference DAG can call native pointers to adjacent edge/vertex objects from the hardware level. The library elements can include a hash table and search algorithm for efficient searching of k-mers (sequence fragments) in the graph while maintaining a very small memory footprint. Through the use of a hash table, the average cost for a lookup may be made to be independent of the number of elements stored in the table. Additionally, the hash table can be implemented to allow for arbitrary insertion or deletion of entries. Use of pointers significantly improves operation for traversing paths through a genomic DAG to retrieve sequence strings or to perform alignments (which traversal operation have traits in common).

In the preferred embodiments, the pointer or native pointer is manipulatable as a memory address in that it points to a physical location on the memory but also dereferencing the pointer accesses intended data. That is, a pointer is a reference to a datum stored somewhere in memory; to obtain that datum is to dereference the pointer. The feature that separates pointers from other kinds of reference is that a pointer's value is interpreted as a memory address, at a low-level or hardware level. The speed and efficiency of the described graph genome engine allows whole genome short-read alignments to be made on genomic-scale genomic reference DAGs containing variant data from thousands of samples, using commercially available, off-the-shelf desktop systems. Such a graph representation provides means for fast random access, modification, and data retrieval. The library can also include and support a universal graph genome coordinate system. The compactness of the graph representation allows the whole human genome along with variants from typical variant databases such as dbSNP to be held and used within the limitations of modern consumer-grade computer systems.

In some embodiments, fast random access is supported and graph object storage are implemented with index-free adjacency in that every element contains a direct pointer to its adjacent elements (e.g., as described in U.S. Pub. 2014/0280360 and U.S. Pub. 2014/0278590, incorporated by reference), which obviates the need for index look-ups, allowing traversals (e.g., as done in the modified SW alignment algorithm described herein) to be very rapid. Index-free adjacency is another example of low-level, or hardware-level, memory referencing for data retrieval (as required in alignment and as particularly pays off in terms of speed gains in the modified, multi-dimensional Smith-Waterman alignment described herein). Specifically, index-free adjacency can be implemented such that the pointers contained within elements are in-fact references to a physical location in memory.

Since a technological implementation that uses physical memory addressing such as native pointers can access and use data in such a lightweight fashion without the requirement of separate index tables or other intervening lookup steps, the capabilities of a given computer, e.g., any modern consumer-grade desktop computer, are extended to allow for full operation of a genomic-scale DAG (i.e., a reference structure that includes not only a complete human genome but also all of the variation in that genome represented in a database such as dbSNP or all of variation discovered by re-sequencing one or more full genomes). Thus storing graph elements (e.g., nodes and edges) using a library of objects with native pointers or other implementation that provides index-free adjacency—i.e., embodiments in which data is retrieved by dereferencing a pointer to a physical location in memory—actually improves the ability of the technology to provide storage, retrieval, and alignment for genomic information since it uses the physical memory of a computer in a particular way.

While no specific format is required for storage of a DAG, FIGS. 1 and 2 are presented to illustrate one convenient and compact format that is useful for illustrations (remembering that in a preferred embodiment, graph objects are stored with index-free adjacency with metadata stored separately to speed traversals and alignments). In illustrations below, exemplary DAGs are presented and discussed as graphs, but it will be appreciated that a DAG qua graph can be translated directly to a data structure in computer memory or a text document and back. Further, while the present disclosure describes the use of DAGs, any graph data structure may be used, including non-directed or non-acyclic graphs, or combinations thereof.

FIG. 1 illustrates using a DAG 101 to represent and manipulate bioinformatic data, such as a plurality of nucleotide sequences. To reveal the contents of DAG 101, FIG. 1 also includes linear listings of a set of hypothetical sequences, each of which are paths through DAG 101. A hypothetical published reference (this could be, for example, the actual genomic DNA from the person from Buffalo, N.Y. that contributed to the "human genome") is included and represents allele 1:

(SEQ ID NO. 1)
5'-CCCAGAACGTTGCATCGTAGACGAGTTTCAGC-3'

A second allele is included (allele 2) that varies from allele 1 bp a 15 bp indel (underlined below):

(SEQ ID NO: 2)
5'-CCCAGAACGTTGCTATGCAACAAGGGACATCGTAGACGAGTTTCAGC-3'

A third allele (allele 3) is also included that matches allele 2 but for a polymorphism in the middle of the indel (in bold) at which an AC from allele 2 is presumptively homologous to a GG in allele 3:

(SEQ ID NO: 3)
5'-CCCAGAACGTTGCTATGCAGGAAGGGACATCGTAGACGAGTTTCAGC-3'

A hypothetical sequence read from a subject is included:

(SEQ ID NO: 4)
5'-TTGCTATGCAGGAAGGGACATCG-3'

In the depicted scenario, the sequence read from the subject has the GG polymorphism (and thus the subject has the GG polymorphism). If the sequence read was aligned to the published reference genome, it would not be discovered that the GG polymorphism represented two consecutive substitutions relative to allele 2. Instead, many existing alignment or assembly algorithms would find no good alignment between the sequence read and the published reference and may even discard that read as failing to satisfy a quality criterion.

Under methods of the invention, a DAG 101 is constructed. Edge 1 is instantiated as 5'-CCCAGAACGTTG-3' (SEQ ID NO: 5). Edge 2 is created as 5'-CATCGTAGACGAGTTTCAGCATT-3' (SEQ ID NO: 6). Edge 3 is CTATGCA. Edge 4 is AAGGGA. Edge 5 is AC and edge 6 is GG. It is worth noting that in some embodiments, mapping reads to a DAG involves creating a new edge to represent data in the reads not yet in the DAG.

For example, prior to read mapping, DAG 101 may not yet include edge 6 (GG). The alignment algorithm (discussed below) finds that the sequence reads best matches the path for allele 2 that connects edges 1→3→5→4→2, as depicted in FIG. 1. To correctly represent the sequence read, new edge 6 is created, and the sequence read is thus represented within DAG 101 by the path that connects edges 1→3→6→4→2. It will be appreciated that prior to this mapping, edges 3, 5, and 4 need not yet exist as separate nodes. Mapping the read and creating the new edge 6 can include breaking up a prior edge of (3+5+4) into edges 3, 5, and 4. That is one of the powerful benefits of using a DAG as a reference—read mapping is not a simple exercise in comparison to a reference, but can include building the reference to represent all known genotypes including novel genotypes only yet documented by new sequence reads.

FIG. 2 shows one possible format of a DAG 101 suited to computational storage and retrieval. DAG 101 as represented in FIG. 2 presents the same topology and sequences as the graphical version depicted in FIG. 1. Here, the depicted format is useful because the nodes are stored as a FASTA file, which is familiar in the art of bioinformatics (and could just as easily be a FASTQ file). The edges can be stored in a text file, here as a simple list.

Arbitrary paths through DAG 101 represent a Markov process as depicted in FIGS. 1 and 2, in that, from any node, upstream nodes are independent of downstream nodes. However, due to genetic conservation, linkage disequilibrium, non-uniform GC content, and other biological phenomenon, following a biologically supported path from node to node through a genomic DAG to represent an actual genome is likely non-Markovian.

A reference DAG can represent a very large number of known variations for a particular genome (or a large number of complete genomes) and methods of the invention can be used to quickly identify a suitable portion or portions of one or a few of those variations or genomes to which a sequence read should be aligned. The following describes methods of indexing collections of data strings (such as nucleotide and protein sequences) represented in a form of directed acyclic graphs (DAGs), and performing efficient searching on the collection including exact and approximate matching techniques. Among other applications, these methods can be used to quickly and efficiently find candidate alignment regions for genomic data sequences (e.g., reads produced by DNA sequencing machines) within genome graphs representing genome data variations.

To identify candidate alignment regions, many small sections, or k-mers, of the DAG can be put into a computer hash function. The hash function calculates an index as a function of the k-mer. The index identifies an entry in a hash table, and the positions of the k-mer within the DAG are stored in that entry, i.e., in the entry indexed by the hash of the k-mer. A sequence read is analyzed by hashing some or all of its k-mers and the corresponding entries of the DAG hash table are accessed to read positions within the DAG where those sequence read k-mers can be found. Sections of the DAG where a threshold number of k-mer positions are found are identified as candidate regions within the represented genomes for alignment or mapping of the sequence read. By the described implementation, a sequence read can be mapped to a "good fit" position within a very large number of reference genomes very rapidly. The following describes a particular embodiment of a method for indexing and subsequently searching a genomic DAG. Among other applications, the described embodiment can be used to quickly and efficiently identify regions of a reference DAG structure to which one might attempt to align reads using a local alignment tool, such as the modified Smith-Waterman algorithm described below. In the described embodiment, a search index is built, after which the search index is searched for candidate regions for local alignment.

Building a Search Index

Populating a hash table for use as a search index according to an embodiment of the disclosure can be performed in the following manner. The method can include identifying a plurality of paths through a reference graph, each path representing a concatenation of the substrings or data strings of genomic sequence and known variation in the genomic sequence stored in objects through the path. In particular, the method uses two parameters, S and B, to segment data strings from a genome graph into a plurality of k-mers, or blocks. (The terms "k-mer" and "block" are used interchangeably in the disclosure.)

First, each path of a plurality of paths through a reference graph or DAG is traced. Tracing of a path results in the identification of a data string (e.g., a nucleotide sequence represented by the path traced), which is added to a collection of data strings for the graph.

Second, for every S-th position of the data strings identified, a hash index and a location identifier are determined for a block of B symbols starting at this position. In this embodiment, the hash index is an unsigned integer number, which is a digest of block data used to verify block data identity. The location identifier can be some information that identifies the exact or approximate position of the block within the graph (typically, the position of the first symbol in the block). For example, the location identifier could be an offset of the block, or its number in the path; a projection of the position of the first, last, or middle symbol in the block onto a particular path (such as the base path) of the graph calculated according to a certain rule; a coordinate of a block's first, last, or middle symbol in a particular graph coordinate system; or any other means of identifying locations within a graph.

Third, the search index is created by listing each identified block's location within the graph in an entry in a table. The table provides hash values of each block and the location identifiers associated with each unique block. (Note that because different paths may contain the same graph edges or portions of the graph, positions of blocks located entirely inside vertices or edges that have already been indexed as parts of other paths are excluded from indexing.) For each identified block, the block location identifier is added to the list of location identifiers corresponding to those determined in step 2. Thus, each entry is indexed according to a hash of that block and contains locations of all blocks having that index.

FIG. 3 provides an illustration of a simple genome graph 301 and Table 1 gives a corresponding simple search index, using parameters S=2 and B=3. In FIG. 3, four possible strings are represented by the graph, as follows (positions of variation in bold):

```
                                              (SEQ ID NO: 7)
            GACATGAGAGTCCAATTCTGATT (SEQ ID NO: 8)
            GACATGAGATTCCAATTCTGATT (SEQ ID NO: 9)
            GACATGAGAGTCCACATGATTCTGATT (SEQ ID NO: 10)
            GACATGAGATTCCACATGATTCTGATT
```

In this example, the location identifiers for blocks in the graph are determined by calculating an offset from the left-most or first position ("0") in the graph (here, representing the nucleotide "G"). Each successive block is assigned an integer location identifier that is incremented by one. Note that as the graph is a multi-dimensional structure, blocks from different data strings may have the same location identifier. However, in certain embodiments, location identifiers may use floating point projections or other means to highlight alternate edges which would have the same offset from the first position in the graph. For example, blocks corresponding to separate paths in the graph could have location identifiers "9" and "9.1", the latter representing an alternate branch. The use of floating point projections is discussed in more detail further below.

To build the search index, with parameters S=2 and B=3, the first block of B nucleotides starting from the first position is identified. That block, or k-mer, is "GAC," and the location identifier for this block is 1. Remembering that every S-th position is to be examined and S=2, the indexing moves forward along the DAG in FIG. 3. from "GAC" to the block "CAT". As the second block identified, the location identifier for block "CAT" is 2.

Figure 4:
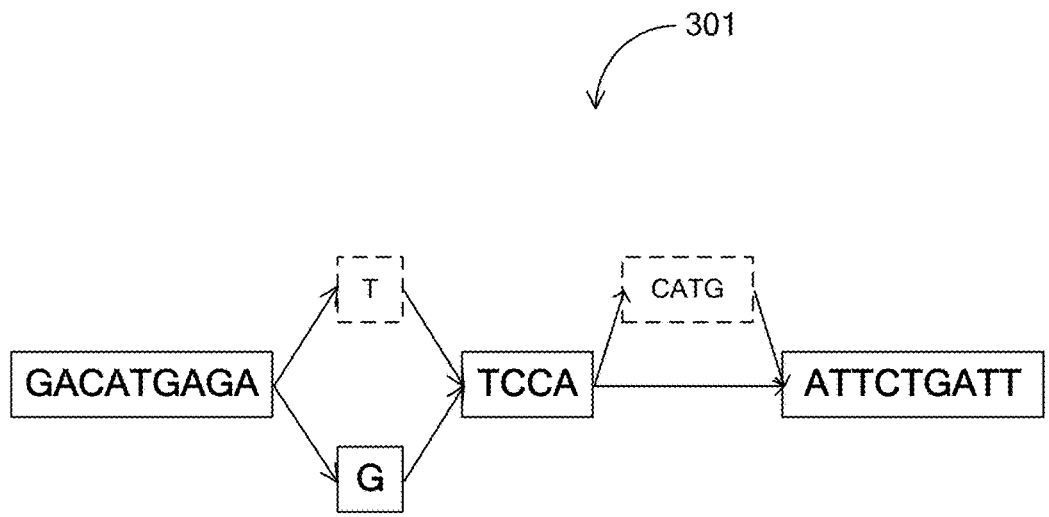
FIG. 4 shows a first path of four that can be traced through the DAG, a data string identified from the path, and a plurality of blocks identified from the data string.

FIG. 4 illustrates the generation of blocks for a first path though the DAG 301 in more detail. In particular, FIG. 4 illustrates the blocks generated from a first path (of four) that can be traced through the DAG 301. The first path is highlighted in bold and identifies the data string GACATGAGAGTCCAATTCTGATT (SEQ ID NO: 7). In this embodiment, this path is referred to as the base path of the DAG 301. (For example, this path and data string could represent the canonical reference sequence of a genome.) As shown in this embodiment, 11 blocks are identified having location identifiers from 1 to 11. Each block comprises a 3-symbol (B=3) sequence taken from every two positions within the data string.

FIG. 5 illustrates the generation of blocks for a second path through the DAG 301. The second path is highlighted in bold and identifies the data string GACATGAGATTCCAATTCTGATT (SEQ ID NO: 8). Similar to the first path, 11 blocks are identified. However, several of the blocks overlap (i.e., they are the same sequence and represent the same portion of the graph) those from the first path. These overlapping blocks are redundant and may be removed from a subsequent indexing step (as highlighted by strike-out). As shown, only block "AGT" having location identifier 5 is new in the second data string.

FIG. 6 illustrates the generation of blocks for a third path through the DAG 301. The third path is highlighted in bold and identifies the data string GACATGAGAGTCCACATGATTCTGATT (SEQ ID NO: 9). Three new blocks are present in the data string: "CAC" (7), "CAT" (8), and "TGA" (9); because they are new, these blocks are not excluded from indexing. Finally, FIG. 7 illustrates the generation of blocks for a fourth and final path through the DAG 301, identifying the data string GACATGAGATTCCACAT-GATTCTGATT (SEQ ID NO: 10). The fourth path includes no new blocks.

Once all of the blocks and location identifiers for the graph have been identified, a search index is created that includes a hash index for the symbols of each unique block and the associated location identifiers for that unique block. For each of these blocks a hash index is calculated, represented in Table 1 as "hash(AGA)" and "hash(AGT)". A hash index is calculated using a hash function, a function that uses a block, or k-mer, as a key, and turns the key into an array index. One suitable method for hashing strings is to map each key to a big integer, i.e., by treating characters of the string of the key as "digits" in a base-α number system, where a is the size of the alphabet in which the string is written. This results in an integer. Where the resulting integers are large enough to exceed the number of slots m in the hash table, this can be addressed by methods that include dividing the integer by a prime and using the remainder (which will distribute the hash values over the m slots). Hash functions are known in the art and are provided within a variety of development environments or languages including Java, Perl, bioPerl, Ruby, bioRuby, C++, etc. In many embodiments and particularly in C and C++, the hash function produces a hash of the value of the block, which hash is the memory address.

Since the hash of a string is an index for an entry in a table, the entry is a place to store information. In the described embodiment, the entry stores the location identifiers for the k-mer that is hashed. Since B=3 and the alphabet for the blocks, or k-mers, is A, T, G, and C, a total of 64 unique blocks are possible. Thus the hash table should include 64 entries. For larger values of B, the number of possible unique blocks is $4^B$. Preferably the hash of NNN where N∈{A, T, G, C} is an integer from 0 to 63 inclusive. That is, in some embodiments, hash(AAA)=0, hash(AAC)=1, hash(AAG)=2, etc., but the precise hash function is not strictly important. In certain embodiments, a built-in hash function is used. The hash value is not represented in Table 1, instead it is being given as "hash(AGA)" or similar.

Table 1 presents a hash table for the DAG in FIG. 3 with S=2 and B=3.

TABLE 1

| Hash Index | Location Identifiers |
|---|---|
| Hash (AGA) | 4 |
| Hash (AGT) | 5 |
| Hash (ATT) | 5, 8, 11 |
| Hash (CAA) | 7 |
| Hash (CAC) | 7 |
| Hash (CAT) | 2, 8 |
| Hash (GAC) | 1 |
| Hash (TCC) | 6 |
| Hash (TCT) | 9 |
| Hash (TGA) | 3, 9, 10 |

In practice, a 1:1 correspondence between unique blocks and hash indices (as depicted in the above example) may not always be feasible given memory constraints. For example, for B=20 and a 4-symbol alphabet (the typical alphabet size for the majority of genomic applications), we would need 4^20 indices, which is far beyond the typical allowance. Therefore, in practice, one may have to use hash functions that do not guarantee 1:1 mapping. The latter may result in hash collisions.

Performing String Searching

The invention provides methods and systems for mapping query sequences, such as sequence reads, to a graph. Obtaining sequence reads is discussed in more detail below. However, it is noted that any subject sequence can be mapped to a DAG including, for example, sequence reads, gene sequences or subsequences, artificial sequences, substrings or entire sequences retrieved in silico (e.g., from GenBank or from the DAG itself), etc. Whatever the subject sequence, the invention provides methods for searching a search index—made as described above—to find regions within the DAG that are candidates for local alignment or mapping of the subject sequence. In a described embodiment, after a search index is built, the search index is used to search for candidate regions for local alignment.

Searching the index for candidate regions for local alignment can include any suitable method. In a preferred embodiment, the subject sequence is hashed at a plurality of positions and the resulting hashes are used to retrieve DAG location identifiers from the search index.

Figure 8:
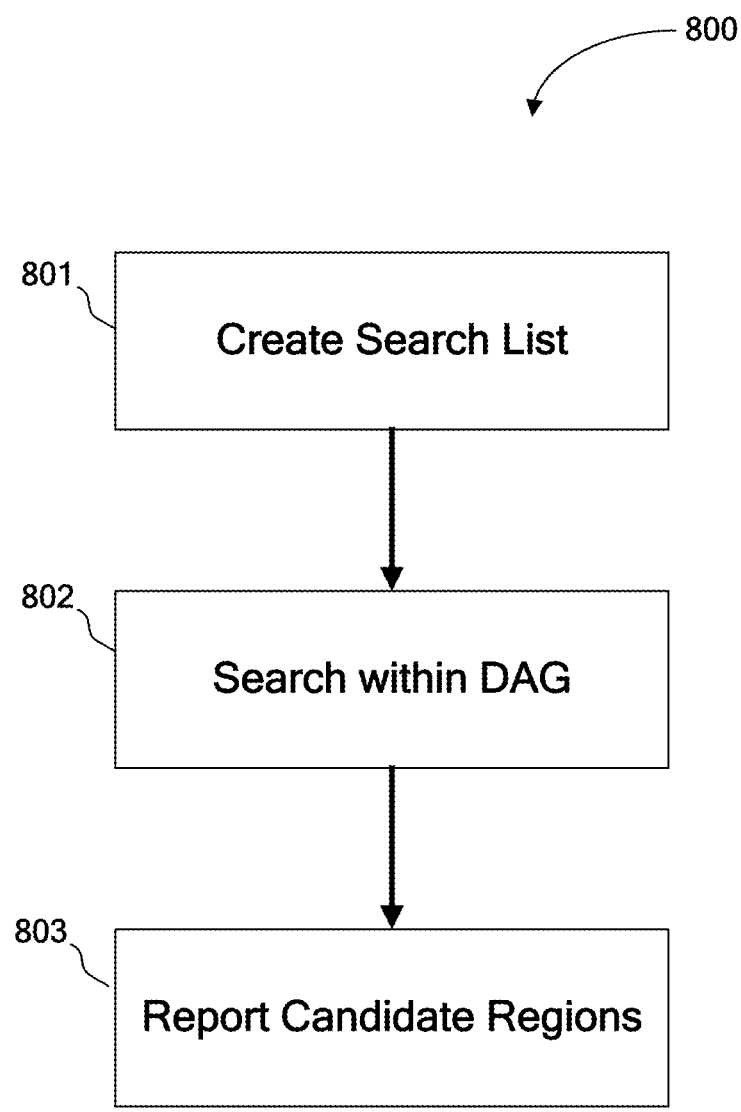
FIG. 8 diagrams a method of mapping a subject sequence to a DAG.

FIG. 8 diagrams a method 800 of mapping a subject sequence to a DAG through the use of a search index. The method of mapping a subject sequence to a DAG includes creating 801 a search list, searching 802 within the DAG (using the search index), and reporting 803 candidate regions.

Creating 801 a "search list" of hash lists can be done by identifying a plurality of query k-mers from the query sequence or sequence read. This can include calculating a hash index (or optionally 2 or 4 indices, as previously noted) for each block of B base pairs in the sequence read, and adding to the search list the entry (hash list) in the DAG hash table corresponding to the calculated index. (This is the equivalent of the process of creating the search index described above, with S set to 1.)

Searching 802 can use a procedure that determines the locations of at least one query k-mer within the graph by reading search index entries indexed according to hashes of query k-mers, and then identifying portions of the graph in which the number of potential matches with different query k-mers is equal to or exceeds a threshold number as candidate targets within the graph for alignment of segments of the query sequence. For example, this can include looking for regions inside the DAG which are similar to the read in size and which contain a substantial number of block matches with the read. An efficient search would leverage the strict order of location identifiers inside hash lists.

One search procedure that leverages the strict order of location identifiers involves the following steps (SS1) through (SS6).

SS1. For each B consecutive symbols of a string being searched for (i.e., a pattern string, such as a nucleotide sequence, sequence read, etc.), a hash index is calculated by applying the hash function used during the search index construction. A list of block location identifiers for each block in the string corresponding to blocks in the calculated search index is determined. (The maximum number of different lists for a string of size M is M−B+1.) This yields an aggregate of location identifier lists, i.e., a list of location identifiers from the search index for each block identified in the pattern string/sequence read.

SS2. Blocks and location identifiers belonging to the aggregate of location identifier lists determined in step SS1 are further analyzed in order to find all different substantial subsets of elements that identify locations within limited continuous regions of the DAG similar to the pattern string in terms of size. These identified limited continuous regions correspond to candidate regions, which may be subsequently used for local alignment. In other words, candidate regions are regions that satisfy a certain length limitation and contain a substantial number of locations identified in the aggregate table. Since location identifiers being analyzed correspond to hash indexes of all continuous string subsequences of size B, chances are high that there will be multiple matches between blocks located in a candidate region and blocks of identical size constituting the pattern string. The larger the number of block matches, the higher the probability of a quality string match.

The region size limitation can be determined a priori based on the length of the pattern string. For exact matching or fuzzy matching without symbol insertions/deletions, a candidate DAG region size will be the same as the size of the pattern string. If insertions/deletions are allowed, the size of the DAG region can be calculated as the size of the pattern string plus the maximum total number of symbols that can be inserted in a string of this size.

Since identifier subsets are determined based on location identifier proximity, significant complexity reduction can be achieved by determining the global order of the location identifiers in the aggregate table and sequentially analyzing the location identifiers in order using a "sliding window" approach. An efficient search procedure would leverage the strict ordering of location identifiers inside individual location identifier lists when determining the global order. One such procedure is outlined below:

a. An initial set of location identifiers is formed by taking the first-in-order (lowest value) location identifier from each list of location identifiers determined in step SS1.

b. During the search the set is updated iteratively. It always includes no more than one element from each list. At each iteration, one of the location identifiers is replaced with the next-in-order location identifier belonging to the same list (i.e., the list that contains the identifier being replaced); this next-in-order identifier is always the smallest identifier among all possible next-in-order identifiers (these are determined by picking one next-in-order candidate from each list if such identifier exists). (It's worth noting that determining of the next-in-order identifier can be done easily and efficiently by creating a heap data structure of all the identifiers belonging to the aggregate of location identifier lists determined in step SS1. The top element in the heap is always the next-in-order element we are looking for.)

c. For each set determined in step SS2.b a maximum number of location identifiers that fall within a continuous DAG region of a certain size is calculated. If the maximum number of location identifiers is above a certain threshold, the DAG region is considered a candidate region.

SS3. Candidate regions identified in step SS2 are further analyzed in order to eliminate false positives. The details of this procedure may differ depending on the specifics of the search algorithm application. Not only the search index, but also the original graph may be used to verify match quality/validity and/or to elaborate on the match details.

SS4. Search results can be reported 803 in a variety of ways. Reporting 803 candidate regions preferably includes reporting location identifiers within the threshold and whether they resulted from matches to "original", inverted, complementary, or inverted complementary blocks. What type of blocks have been matched is important because certain combinations of block types are more biologically plausible than others. Optionally, candidates can be reported ranked according to a score based on number of blocks matched and different weights for different types of blocks and combinations. Similarly, search results can be reported in a form of a list of candidate regions, or a list of matching graph paths. Depending on the requirements, the report may include location of the candidate region in the DAG, length of the candidate region, graph path specification, number of block matches, location of the matching blocks, weighted candidate rank, etc.

SS5. (Optional) Search results may be ordered by match quality. For example, matches with higher numbers of block matches or higher weighted candidate ranks will be reported first.

SS6. (Optional) For each result reported in step SS4 an additional refining step or steps can be applied in order to obtain more detailed information about the match. When performing DNA sequencing one may want to apply a local alignment procedure right after a global read location has been determined with the use of the described method.

Figure 9:
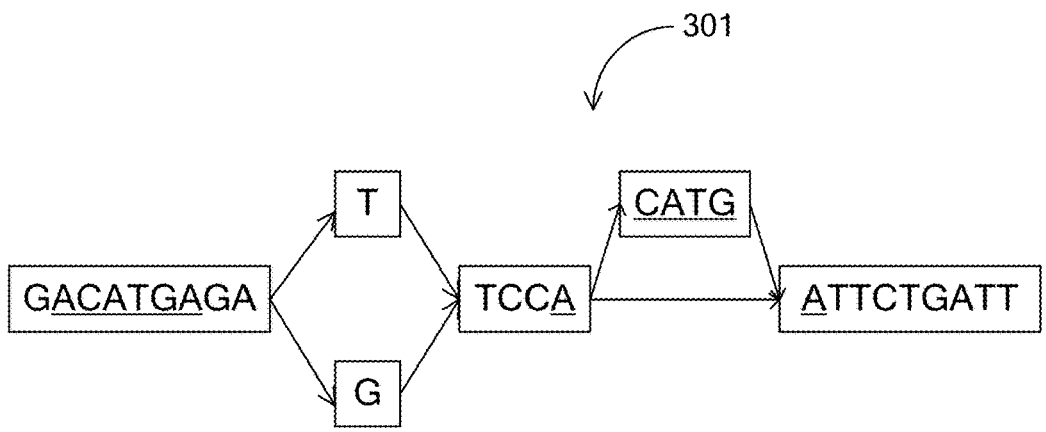
FIG. 9 illustrates the location of a pattern string ACATGA in a DAG.

The following example illustrates the described string search procedure. It finds all occurrences of the string ACATGA in the DAG used in the above search index construction example (i.e., using exact string matching). FIG. 9 illustrates the occurrences (underlined) of the pattern string ACATAG in the DAG 301.

Using a block size B=3, the continuous subsequences (i.e., blocks) of the string ACATGA are: ACA, CAT, ATG, and TGA. We then create a new table, an aggregate of location identifier lists (from step SS1 above), comparing the location identifiers in the search index for the DAG (in Table 1) with the blocks identified from the pattern string. The location identifiers for hashed indexes are noted in a search list, as shown in Table 2, below:

TABLE 2

| Hash Index | Location Identifiers |
|---|---|
| Hash (ACA) | — |
| Hash (ATG) | — |
| Hash (CAT) | 2, 8 |
| Hash (TGA) | 3, 9, 10 |

The blocks and location identifiers are then analyzed to determine candidate regions for alignment (i.e., step SS2). In particular, blocks having location identifiers are identified as block matches (i.e., an "X" in Table 3, below.) In this example, blocks that occur in sequentially ordered location identifiers are noted as candidate regions for string matching and subsequent local alignment.

TABLE 3

| | Location Identifiers (Global Ordering) | | | | | | | | | |
|---|---|---|---|---|---|---|---|---|---|---|
| Hash Index | 1 | 2 | 3 | 4 | 5 | 6 | 7 | 8 | 9 | 10 |
| Hash (ACA) | | | | | | | | | | |
| Hash (ATG) | | | | | | | | | | |
| Hash (CAT) | | X | | | | | | X | | |
| Hash (TGA) | | | X | | | | | | | X |

The size of the pattern string (ACATGA) is six. In this example, taking into account the block size (B=3) and block step (S=2), no more than two consecutive identifiers can constitute a subset corresponding to a candidate region; i.e., the size of an "analysis window" is 2. There are two subsets of location identifiers that satisfy this requirement, as shown in Table 3: {2,3} and {8,9}. These subsets correspond to two different candidate DAG regions. The exact region offsets can be determined by analyzing offsets of matching blocks in the pattern string: CAT (offset=1), TGA (offset=3). The region that corresponds to subset (2,3} has offset 2×(2−1)−1=1 and the region that corresponds to subset {8,9} has offset 2×(8−1)−1=13 (offsets are 0-based).

In certain embodiments, the number of block matches within an analysis window can vary or not be consecutive. Preferably, the number of block matches within an analysis window or interval within the global ordering sufficient to constitute a candidate mapping region (referred to herein as a substantial number, predetermined number, or threshold number) will be a value in which there is a small probability that a number of k-mers or block matches are positioned close to one another simply by chance, and not because they constitute a valid match. For example, consider three k-mers of length 5 (B=5) positioned within an interval of 100 nucleotides. The number of different combinations of 15 nucleotides (i.e., 3 k-mers of length 5) is 4^15 (approximately 1 billion). This value is on the same scale as the size of the human genome. So, finding three k-mers of length 5 within an interval of 100 base pairs may simply be a coincidence. In this case, the substantial number of block matches within an interval to constitute a candidate mapping region may be increased to yield candidate regions that are less likely to be a product of chance. Accordingly, increasing the number of block matches sufficient to constitute a candidate region increases the specificity of matches, at a loss of sensitivity.

In certain embodiments, the parameters of S, B, and the size of the analysis window for identifying a substantial number of location identifiers constituting a subset corresponding to a candidate region can vary. In particular, the invention includes insights regarding optimal configurations of parameters such as S and B. For example, when configuring parameters, a smaller block step (S) value results in more frequent "sampling" of the path, but a correspondingly larger search index. A larger block size (B) makes for more precise matches of individual blocks (i.e., a longer search index, with each hash value having a correspondingly shorter list of location identifiers associated with it), but makes it harder to match shorter reads. However, a smaller block size (B) allows for a higher likelihood of matching blocks from the pattern string to those in the index. In general, selecting smaller parameters improves efficiency, but also results in slower processing and excessive memory consumption, as the average length of the location identifier list increases.

The ratio between S and B determines the "coverage": if S=B, blocks being indexed while processing a path do not overlap, if S=½ B then each symbol of the path will be represented in 2 blocks, if S=¼ B symbol will be represented in 3 blocks, etc. Our experiments show that S=½ B works very well in a general situation; though, it may not be optimal for some specific applications. The choice of block size highly depends on alphabet size and memory requirements. For DNA sequencing, preferable values of B are within the interval [8, 14].

The disclosed search procedure has many advantages. First, it can efficiently locate string matches split into multiple segments. These segments can be arbitrarily permuted and/or inverted. This property makes the method extremely efficient for paired-end DNA sequencing. Second, a matching string should not necessarily be a part of a single graph path. The search procedure can find split matches with match segments located on completely different paths. These paths may overlap with different branches within a single region of the graph. Third, search does not require keeping the original graph. In many cases, match location can be determined by just analyzing the location identifiers of identified block matches. Fourth, the trade-off among processing speed, search efficiency and memory consumption can be varied in very wide ranges by properly selecting parameters S and B (parameter adjustment is discussed below). An implementation of the method can be very efficient in terms of speed and memory consumption, or very efficient in terms of search efficiency, or deliver a certain compromise. One particular advantage of this search method over FM-index based methods is that only the hash lists for indices on the search list are operated on. Since these can easily be stored in memory, the much larger hash table can be left on disk and the search can be run with only one read operation, minimizing I/O. Finally, since only a very limited number of location identifier lists are analyzed when processing each string, a search index should not necessarily be entirely kept in operating memory. The index can be stored on an external storage device with a very large capacity (e.g., HDD/SDD drives, network etc.) so that only selected location identifier lists are loaded into the operating memory. By intelligently leveraging caching and prefetching techniques it is possible to overcome typical speed limitations of external storage (e.g., high latency of random data access). It is important to note, that this approach is fully consistent with concepts of batch processing and horizontal scaling. Thus, implementation of the proposed method can very efficient in terms of operating memory consumption. (We should also take into account the fact the search procedure does not necessarily require keeping the original data.) This makes the method applicable to extremely large collections of strings.

Use of Floating Point Projections to a Branch as Location Identifiers

Genome graphs are complex structures which describe a variety of genomic variation, including structural variations such as large insertions and deletions. These variations can be addressed by optionally employing a variation on the described search index and location identifiers in which floating-point position indicators are used. It may be found that the above-described methods can be further optimized for long indels or other structural variants. For example, it may be suspected that long insertions and deletions create "mismatched" location identifiers among different paths.

In certain embodiments, "floating point" location identifiers are used for sections of the DAG in which an alternate path has more base pairs than the corresponding section of the reference path. Floating point location identifiers provide one approach to mapping structural variants, as will be appreciated by one of skill in the art; these are discussed below.

Thus it can be seen that the invention provides methods for representing a large amount of, and large variety of genetic reference information using a DAG. In fact, a genomic reference DAG according to the invention may be used to represent all of the genetic variety existing among a large plurality of related genomes, including both small mutations such as SNPs and structural variants such as indels or transposons.

Figure 10A:
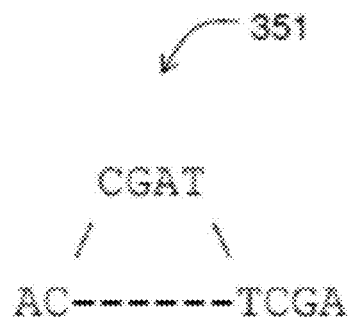
FIG. 10A presents an exemplary DAG for consideration.

As previously noted, location identifiers based on an offset from the first position of a graph may lead to situations in which different positions in the graph may have the same location identifier. This can be avoided by using a location identifier scheme in which a divergent branch uses a modified location identifier, such as floating point projection. FIG. 10A presents an exemplary DAG 351 for consideration in connection with the following example. In this example, the object is to build a search index for the DAG 351. DAG 351 contains, among others, paths representing a data string ACCGATTCGA (SEQ ID NO: 11). For convenience, this branch will be dubbed the "base path" in the example that follows. The illustrated process includes using parameters S=2, B=2 and block number as a block location identifier.

After enumerating two different paths, two different blocks may have the same location identifier. For example, in a DAG including a large structural variant along one branch, the position of nucleotides after the insertion may end up numbered quite differently depending on which path is taken. Since location identifiers in the search index are not path-specific, a match between a block on the search list and a block in the post-insertion section of the DAG will result in "hits" at rather disparate positions.

Figure 10B:
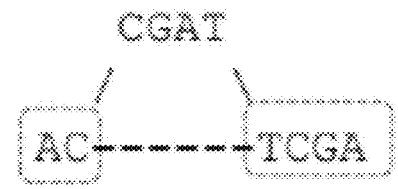
FIG. 10B illustrates a first path through the DAG.
Figure 10C:
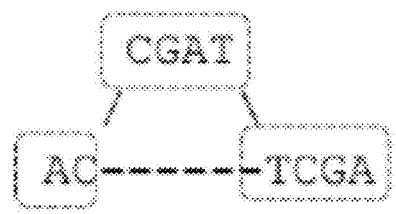
FIG. 10C illustrates a second path through the DAG.
Figure 10D:
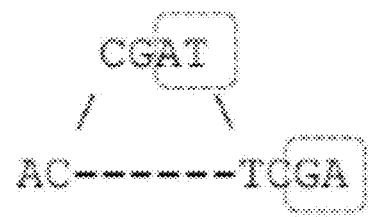
FIG. 10D illustrates the placement of two blocks in the DAG.

FIG. 10B illustrates a first path through the DAG 351 corresponding to the data string ACTCGA (SEQ ID NO: 12). FIG. 10C illustrates a second path through the DAG 351, corresponding to the data string ACCGATTCGA (SEQ ID NO: 13). FIG. 10D illustrates the position of two blocks, AT and GA, and their position in the DAG 351. Those instances of blocks AT and GA have the same identifier: 3 (note that in this example, location identifiers are 0-based). Although the location identifier is the same, these blocks are actually located only slightly away (i.e., a few base pairs) from each other. However, if the alternative branch was much longer (e.g., hundreds or thousands of symbols), the distance between blocks sharing the same location identifier could be much larger. This may become a serious issue during the search, and especially when determining the offsets of the candidate regions.

Figure 11:
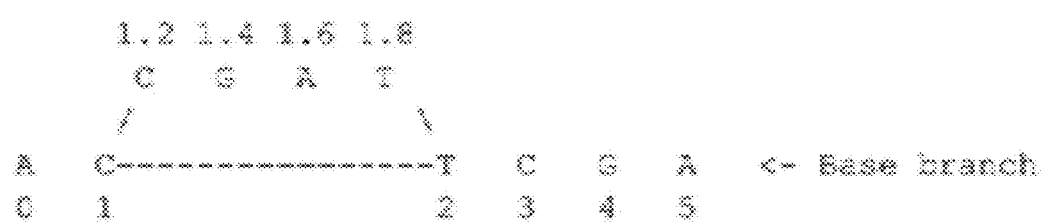
FIG. 11 illustrates the use of floating-point projections of block start positions.

As a workaround, instead of block numbers one could use floating-point projections of block start positions onto one of the branches or paths (such as the base path). FIG. 11 illustrates the use of floating-point projections of block start positions onto one of the paths, i.e., the base path, of DAG 351. The block location identifiers of the base path include AC (0), TC (2), and GA (4). The block location identifiers for the alternative path include CG (1.2) and AT (1.6). This alternative approach is more consistent with the concept of graph regions since, unlike block numbers, similar projections will always belong to the same region. (It is important to note that in this case the region corresponds to an interval on the base path and, thus, shall be specified using base path coordinates.

Application to Paired-End Sequence Read Alignment

The above-described searching scheme can apply to both single-end and paired-end sequencing data. Much of the highest-quality and most prevalent short read sequencing data takes the form of paired-end data. Such reads arise when a fragment of nucleic acid is read from both ends. As the quality of a read often deteriorates as the distance from the origin of the read increases, we are left with two "paired-end mates." The situation that results is one in which one has two short reads and can be confident that those reads arise from locations in the genome a certain distance apart (perhaps, for example, 300 base pairs).

U.S. Pat. No. 9,092,402, U.S. Pat. No. 9,063,914, U.S. Pub. 2015/0112602, and U.S. Pub. 2015/0112658—each incorporated by reference—describe challenges with paired-end data and new approaches to the effective analysis of that data. Methods of the invention provide an example of using information from each mate in a pair "simultaneously," the advantages of which are covered in other disclosures, and can also be applied using other alignment mechanisms such as the extended Smith-Waterman approach described in U.S. Pat. No. 9,092,402, U.S. Pat. No. 9,063,914, U.S. Pub. 2015/0112602, U.S. Pub. 2015/0057946, and U.S. Pub. 2015/0112658, as well as in detail below.

Figure 12:
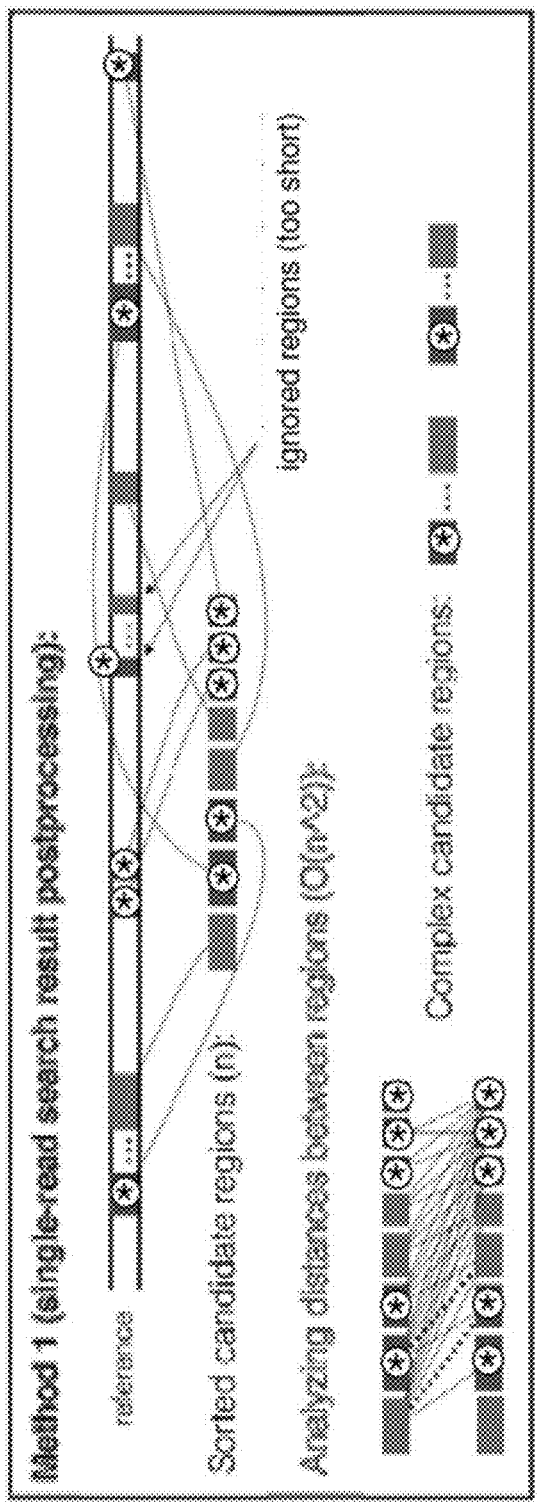
FIG. 12 depicts aspects of a method for single-read analysis.

FIG. 12 depicts aspects of single-read search result post-processing of paired-end sequence data. In the standard approach towards paired-end alignment, each end (or "mate") of a paired-end read is aligned separately, and then the locations of the alignments of each mate are compared to identify where the mates have been aligned within the appropriate distance of one another and with the appropriate orientation. In the approach depicted in FIG. 12, one may imagine trying to find a good alignment of a set of paired-end mates (any 'left-hand' mate is adorned with an asterisk and any 'right-hand' mate is not so adorned; one might substitute '5-prime' and '3-prime' for 'left-hand' and 'right-hand' in many contexts).

This status quo is problematic in several respects. The first filtering stage produces many false positives: in locations where only one of a pair of mates closely resembles some part of a target genome or part of a genome, computational effort is expended in identifying and storing the match, and the possibility of error is introduced, just as it would be if we matched the first half of a (non-paired-end) read without regard to the second half of that read.

These false positives are particularly damaging from the point of view of computational efficiency, because the location of each match for each mate is compared with the location of each match for the other mate. That is, the process whereby the first set of matches are analyzed with respect to distance between elements of a pair is $O(n^2)$ in the number of candidates identified in the first filtering stage. Although bioinformatic data, and the contexts within which that data is used, are richly varied, it is generally reasonable to assume that the data will be large enough that $O(n^2)$ algorithms will cause significant problems, either in their feasibility or the cost of their implementation.

The first filtering stage also produces false negatives: it can happen that although neither mate in a pair aligns closely enough to the reference to pass through the first filtering stage, the aggregate alignment of both mates is of sufficiently high quality to merit attention. Once again, the analysis of a paired-end mate pair into its two mates creates situations in which ignoring the relationship between the mates at an early stage introduces error into the process.

Figure 13:
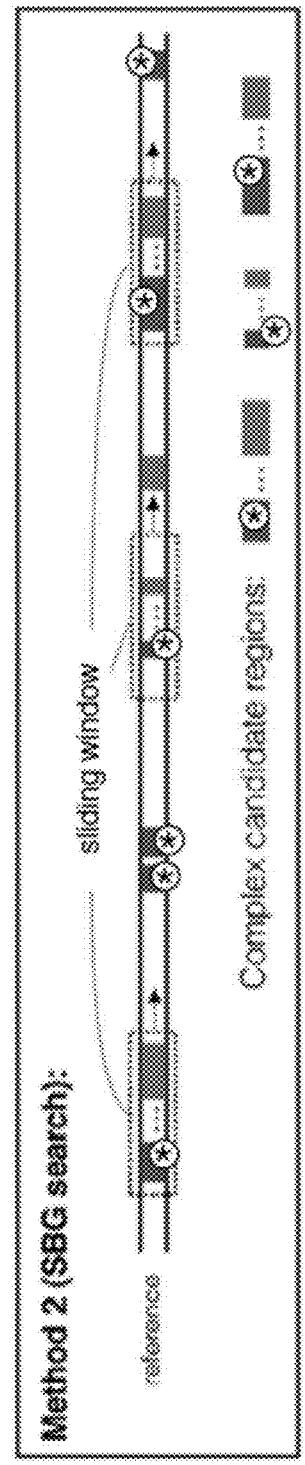
FIG. 13 illustrates a sliding window technique.

In contrast, methods of the invention can be used to apply a sliding window approach to identify candidate locations for paired-end alignment. FIG. 13 briefly illustrates the sliding window technique. In FIG. 13, a window of size N is moved along the reference. Regions in which a substantial number of block matches are identified for both the 5' and 3' ends of the read are noted. As there is no second stage of comparing the left- and right-hand proto-alignments, we skip the expensive $O(n^2)$ step and immediately find candidate regions.

Figure 14:
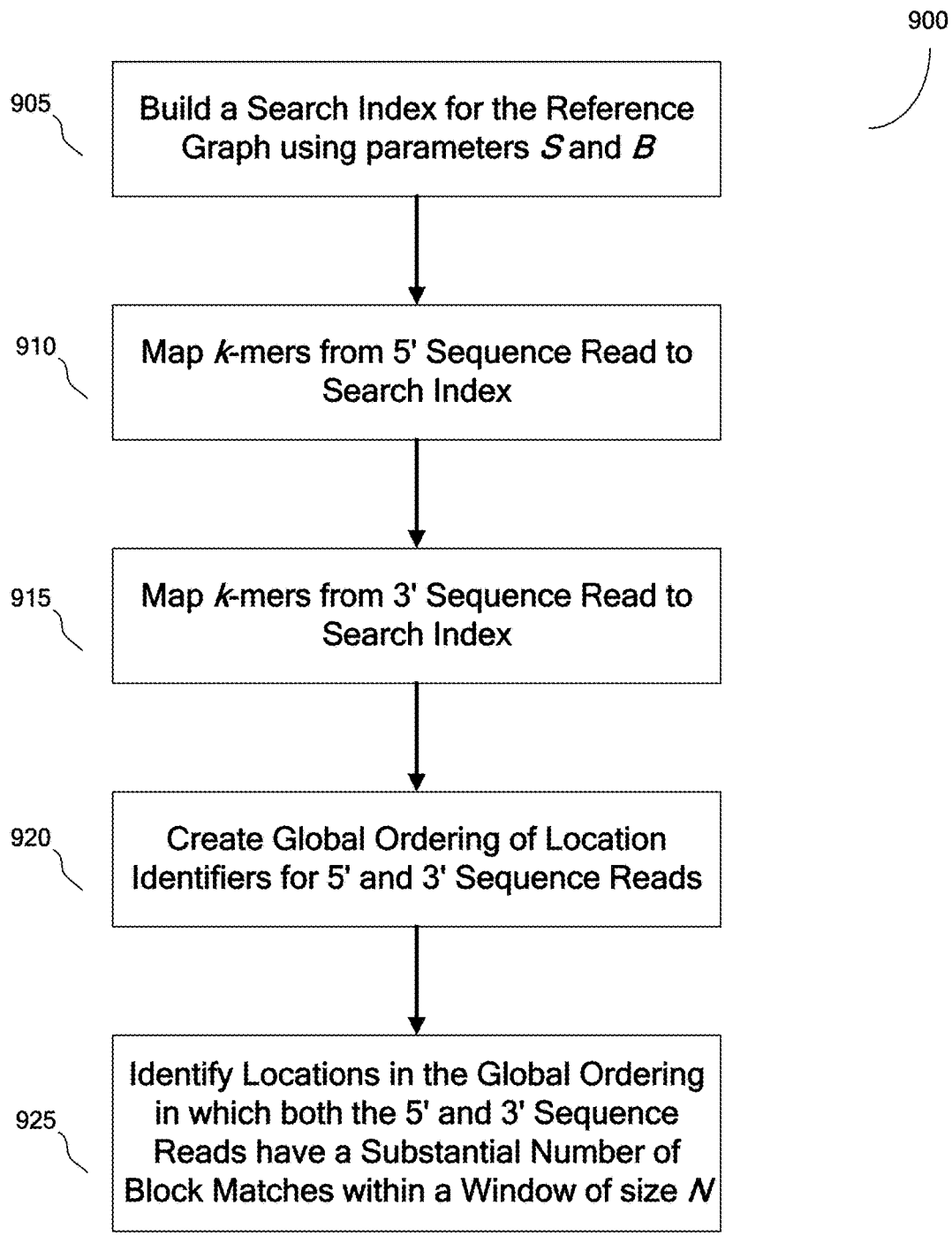
FIG. 14 depicts an exemplary method for mapping a paired-end read to a reference graph according to an embodiment of the disclosure.

FIG. 14 depicts an exemplary method 900 of performing a paired-end alignment of a sequence read against a reference graph using a sliding window technique according to an embodiment of the disclosure. The method 900 can begin by building a search index for the reference graph using parameters S and B (e.g., as described with respect to Table 1, above) (step 905). K-mers from each pair of the sequence read (i.e., the 5' and 3' ends) are identified and mapped to the search index to yield a list of location identifiers for each (e.g., as previously described with respect to Table 2) (steps 910, 915). These identified location identifiers are then used to create a global ordering of location identifiers (e.g., as described with respect to Table 3, above) (step 920). The method 900 then proceeds by identifying locations in the global ordering in which both the 5' and 3' sequence reads have a substantial number of block matches within a sliding window of size N.

The size of the sliding window (i.e., the value of N) can vary depending on the type of paired-end read. For example, Illumina paired-end reads typically have an inferred DNA fragment size of less than 1000 base pairs, and more commonly between 200 and 600 base pairs. In these cases, a window size of 1000 or less may be suitable. However, mate-pair libraries may have an inferred fragment size in excess of 5000 base pairs (i.e., due to circularization and ligation steps associated with mate-pair library construction; the actual DNA molecule will still likely have a size of between 200 and 600 base pairs). In these cases, a larger window size is warranted. This is in contrast to single read data, in which the size of an analysis window may be about the length of the sequence read (as previously described).

In certain embodiments, a technique is used that treats the entire paired-end item (two reads with a gap between them) as a single unit to be aligned. This is conceptually continuous with the treatment of non-paired-end data: just as we do not align each half of a continuous read separately and then construct full reads by imposing spatial constraints on the half-alignments, we do not align the mates separately. Rather, we use the "sliding window" (or "look-back interval") approach, treating both reads as a single input. In applying the sliding-window/look-back search technique to the paired-end problem, the reference sequence is scanned for suitable complex matches, i.e., matches in which the k-mer searched for includes more than just symbols to be matched and symbols representing a gap between the mates.

There are several kinds of ways to implement such a technique. In one embodiment, the two mates are joined with 'wildcard' characters that are considered to match any base pair and then align the filled-in read. Both the sliding-window/lookback approach and other standard alignment methods (e.g., any method based on Smith-Waterman or a related algorithm) could then be applied straightforwardly.

Further, it is noted that nothing about the previous discussion limits the technique to sets of two mates. In situations where three, four, or arbitrarily many reads are related, the technique is usable mutatis mutandis. Additionally and alternatively it may be preferable to use the sliding window technique described herein for the analysis of one or more scaffolds. For the purposes of this discussion, "scaffold" refers to an arrangement of contigs, i.e., a scaffold provides information about the relative orientation and positioning of a set of contigs. A contig (from contiguous) is a set of overlapping DNA segments that together represent a contiguous region of DNA. The described sliding window technique may be extended to be used for aligning a scaffold to a reference DAG or reference genome, or possibly to align one scaffold to another.

Applications

As noted above, methods of the invention can be used to map any suitable subject sequence to a reference DAG representing a plurality of known genomes. In certain embodiments, the subject sequences are sequence reads (e.g., from an NGS sequencing instrument), and methods are used to map the sequence reads to the reference DAG. Mapping generally refers to finding a location within a reference that exhibits a certain biological relationship with the reference, the biological relationship of interest usually being identity or homology. Mapping can include performing a pairwise alignment between the subject sequence (e.g., sequence read) and the location within the reference. The output of mapping can include a pairwise alignment, some kind of summary such as a CIGAR string (discussed elsewhere herein) or sequence alignment map (SAM) or binary alignment map (BAM), or mutation calling, or other outputs known in the art.

In certain embodiments, sequence reads are obtained by performing sequencing on a sample from a subject. Sequencing may be by any method known in the art. See, generally, Quail, et al., 2012, A tale of three next generation sequencing platforms: comparison of Ion Torrent, Pacific Biosciences and Illumina MiSeq sequencers, BMC Genomics 13:341. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. No. 5,583,024; U.S. Pat. No. 5,674,713; and U.S. Pat. No. 5,700,673, the contents of which are incorporated by reference herein in their entirety. 454 sequencing involves two steps. In the first step of those systems, DNA is sheared into blunt-end fragments of approximately 300-800 base pairs attached to DNA capture beads and then amplified within droplets of an oil-water emulsion. In the second step, pyrosequencing is performed on each DNA fragment in parallel. Addition of one or more nucleotides generates a light signal that is recorded by a CCD camera in a sequencing instrument.

Another example of a DNA sequencing technique that can be used is SOLiD technology by Applied Biosystems from Life Technologies Corporation (Carlsbad, Calif.). In SOLiD sequencing, genomic DNA is sheared into fragments, and adaptors are attached to the 5' and 3' ends of the fragments to generate a fragment library. Clonal bead populations are prepared in microreactors containing beads, primers, template, and PCR components. Following PCR, the templates are denatured and enriched and the sequence is determined by a process that includes sequential hybridization and ligation of fluorescently labeled oligonucleotides.

Another example of a DNA sequencing technique that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, each incorporated by reference. DNA is fragmented and given amplification and sequencing adapter oligos. The fragments can be attached to a surface. Addition of one or more nucleotides releases a proton ($H^+$), which signal is detected and recorded in a sequencing instrument.

Another example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. No. 7,960,120, U.S. Pat. No. 7,835,871, U.S. Pat. No. 7,232,656, U.S. Pat. No. 7,598,035, U.S. Pat. No. 6,306,597, U.S. Pat. No. 6,210,891, U.S. Pat. No. 6,828,100, U.S. Pat. No. 6,833,246, and U.S. Pat. No. 6,911,345, each incorporated by reference.

Other examples of a sequencing technology that can be used include the single molecule, real-time (SMRT) technology of Pacific Biosciences (Menlo Park, Calif.) and nanopore sequencing as described in Soni and Meller, 2007 Clin Chem 53:1996-2001.

Sequencing generates a plurality of reads. Reads generally include sequences of nucleotide data less than about 600 or 700 bases in length and methods of the invention may be applicable to reads or sequence information of any length including, e.g., reads of <150 bases or even less than 50, as well as greater than 700, e.g., thousands of bases in length. Typically, NGS reads are either mapped to a reference or assembled de novo and analyzed.

As discussed above, methods of the invention include mapping NGS reads to a reference that is a genomic directed acyclic graph (DAG) or similar data structure. The methods described above allow candidate regions of a reference DAG to be found very quickly, where a candidate region is a substring of a path within a DAG for which there is evidence of a meaningful biological relationship—such as homology, identity, or duplication—between the sequence read and the candidate region. While finding a candidate region is a valuable and useful objective in and of itself, the invention further includes methods of aligning the subject sequence read to the candidate region.

Using alignment algorithms of the invention, reads can be rapidly mapped despite their large numbers. Numerous benefits obtain by using a DAG as a reference. For example, aligning against a DAG is more accurate than aligning against one reference and then attempting to adjust one's results in light of other extrinsic information. This is primarily because the latter approach enforces an unnatural asymmetry between the sequence used in the initial alignment and other information: aligning against a reference that already includes or reflects many sequences allows us to treat them on a par, whereas a reference that contains only one linear sequence must in general treat that sequence in a different way from how it treats other sequences. Aligning against an object that potentially represents all the relevant physical possibilities is much more computationally efficient than attempting to align against a linear sequence for each physical possibility (the number of such possibilities will generally be exponential in the number of junctions).

Embodiments of the invention include aligning one or more reads against the DAG.

Pairwise alignment generally involves placing one sequence along part of target, introducing gaps according to an algorithm, scoring how well the two sequences match, and preferably repeating for various position along the reference. The best-scoring match is deemed to be the alignment and represents an inference about what the sequence data represents. In some embodiments, scoring an alignment of a pair of nucleic acid sequences involves setting values for the probabilities of substitutions and indels. When individual bases are aligned, a match or mismatch contributes to the alignment score by a substitution probability, which could be, for example, 1 for a match and −0.33 for a mismatch. An indel deducts from an alignment score by a gap penalty, which could be, for example, −1. Gap penalties and substitution probabilities can be based on empirical knowledge or a priori assumptions about how sequences evolve. Their values affects the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (i) |x'|=|y'|; (ii) removing spaces from x' and y' should get back x and y, respectively; and (iii) for any i, x'[i] and y'[i] cannot be both spaces.

A gap is a maximal substring of contiguous spaces in either x' or y'. An alignment A can include the following three kinds of regions: (i) matched pair (e.g., x'[i]=y'[i]; (ii) mismatched pair, (e.g., x'[i]≠y'[i] and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

In some embodiments, any pair has a score a defined by a 4×4 matrix B of substitution probabilities. For example, $B(i,i)=1$ and $0<B(i,j)_{i< >j}<1$ is one possible scoring system. For instance, where a transition is thought to be more biologically probable than a transversion, matrix B could include B(C,T)=0.7 and B(A,T)=0.3, or any other set of values desired or determined by methods known in the art.

Alignment according to some embodiments of the invention includes pairwise alignment. A pairwise alignment, generally, involves—for sequence Q (query) having m characters and a reference genome T (target) of n characters—finding and evaluating possible local alignments between Q and T. For any $1 \leq i \leq n$ and $1 \leq j \leq m$, the largest possible alignment score of T[h . . . i] and Q[k . . . j], where $h \leq i$ and $k \leq j$, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48(3):443-453, 1970) and Smith-Waterman (J Mol Biol, 147(1):195-197, 1981; Adv. in Math. 20(3), 367-387, 1976). A further improvement to Smith-Waterman by Gotoh (J Mol Biol, 162(3), 705-708, 1982) reduces the calculation time from $O(m^2n)$ to $O(mn)$ where m and n are the sequence sizes being compared and is more amendable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon's cloud computing resources. All of the journal articles referenced herein are incorporated by reference in their entireties.

The Smith-Waterman (SW) algorithm aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

In some embodiments, pairwise alignment proceeds according to dot-matrix methods, dynamic programming methods, or word methods. Dynamic programming methods generally implement the Smith-Waterman (SW) algorithm or the Needleman-Wunsch (NW) algorithm. Alignment according to the NW algorithm generally scores aligned characters according to a similarity matrix S(a,b) (e.g., such as the aforementioned matrix B) with a linear gap penalty d. Matrix S(a,b) generally supplies substitution probabilities. The SW algorithm is similar to the NW algorithm, but any negative scoring matrix cells are set to zero. The SW and NW algorithms, and implementations thereof, are described in more detail in U.S. Pat. No. 5,701,256 and U.S. Pub. 2009/0119313, both herein incorporated by reference in their entirety.

An alignment program that implements a version of the Smith-Waterman algorithm is MUMmer, available from the SourceForge web site maintained by Geeknet (Fairfax, Va.). MUMmer is a system for rapidly aligning genome-scale sequences (Kurtz, S., et al., Genome Biology, 5:R12 (2004); Delcher, A. L., et al., Nucl. Acids Res., 27:11 (1999)). For example, MUMmer 3.0 can find all 20-basepair or longer exact matches between a pair of 5-megabase genomes in 13.7 seconds, using 78 MB of memory, on a 2.4 GHz Linux desktop computer. MUMmer can handle the 100s or 1000s of contigs from a shotgun sequencing project, and will align them to another set of contigs or a reference using the NUCmer program included with the system. If the species are too divergent for a DNA sequence alignment to detect similarity, then the PROmer program can generate alignments based upon the six-frame translations of both input sequences.

Other exemplary alignment programs include: Efficient Large-Scale Alignment of Nucleotide Databases (ELAND) or the ELANDv2 component of the Consensus Assessment of Sequence and Variation (CASAVA) software (Illumina, San Diego, Calif.); RTG Investigator from Real Time Genomics, Inc. (San Francisco, Calif.); Novoalign from Novocraft (Selangor, Malaysia); Exonerate, European Bioinformatics Institute (Hinxton, UK) (Slater, G., and Birney, E., BMC Bioinformatics 6:31 (2005)), Clustal Omega, from University College Dublin (Dublin, Ireland) (Sievers F., et al., Mol Syst Biol 7, article 539 (2011)); ClustalW or ClustalX from University College Dublin (Dublin, Ireland) (Larkin M. A., et al., Bioinformatics, 23, 2947-2948 (2007)); and FASTA, European Bioinformatics Institute (Hinxton, UK) (Pearson W. R., et al., PNAS 85(8):2444-8 (1988); Lipman, D. J., Science 227(4693):1435-41 (1985)).

As discussed above, it may be preferable or desirable to implement the SW alignment algorithm or a modified version of (discussed in greater detail below) when aligning sequences to a direct acyclic annotated reference genome.

The SW algorithm is easily expressed for an n×m matrix H, representing the two strings of length n and m, in terms of equation (1) below:

$$H_{k0}=H_{0l}=0 \text{ (for } 0\le k\le n \text{ and } 0\le l\le m) \tag{1}$$

$$H_{ij}=\max\{H_{i-1,j-1}+s(a_i,b_j),H_{i-1,j}-W_{in},H_{i,j-1}-W_{del},0\}$$

(for $1\le i\le n$ and $1\le j\le m$)

In the equations above, $s(a_i,b_j)$ represents either a match bonus (when $a_i=b_j$) or a mismatch penalty (when $a_i\ne b_j$), and insertions and deletions are given the penalties $W_{in}$ and $W_{del}$, respectively. In most instances, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values $H_{i-1,j-1}$, $H_{i-1,j}$, or $H_{i,j-1}$ was used to compute the final maximum value for each cell. The backtracking stops when a zero is reached. The optimal-scoring alignment may contain greater than the minimum possible number of insertions and deletions, while containing far fewer than the maximum possible number of substitutions.

When applied as SW or SW-Gotoh, the techniques use a dynamic programming algorithm to perform local sequence alignment of the two strings, S and A, of sizes m and n, respectively. This dynamic programming technique employs tables or matrices to preserve match scores and avoid re-computation for successive cells. Each element of the string can be indexed with respect to a letter of the sequence, that is, if S is the string ATCGAA, S[1]=A.

Instead of representing the optimum alignment as $H_{i,j}$(above), the optimum alignment can be represented as B[j,k] in equation (2) below:

$$B[j,k]=\max(p[j,k],i[j,k],d[j,k],0) \text{ (for } 0<j\le m, 0<k\le n) \tag{2}$$

The arguments of the maximum function, B[j,k], are outlined in equations (3)-(5) below, wherein MISMATCH_PEN, MATCH_BONUS, INSERTION_PEN, DELETION_PEN, and OPENING_PEN are all constants, and all negative except for MATCH_BONUS (PEN is short for PENALTY). The match argument, p[j,k], is given by equation (3), below:

$$p[j,k] = \max(p[j-1,k-1], i[j-1,k-1], d[j-1,k-1]) + \tag{3}$$

$$\text{MISMATCH\_PEN, if } S[j] \ne A[k] =$$

$$\max(p[j-1,k-1], i[j-1,k-1], d[j-1,k-1]) +$$

$$\text{MATCH\_BONUS, if } S[j] = A[k]$$

the insertion argument i[j,k], is given by equation (4), below:

$$i[j,k]=\max(p[j-1,k]+\text{OPENING\_PEN},i[j-1,k],d[j-1,k]+\text{OPENING\_PEN})+\text{INSERTION\_PEN} \tag{4}$$

and the deletion argument d[j,k], is given by equation (5), below:

$$d[,i,k]=\max(p[,i,k-1]+\text{OPENING\_PEN}, i[,i,k-1]+\text{OPENING\_PEN}, d[,j,k-1])+\text{DELETION\_PEN} \quad (5)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: *Bio-Sequence Comparison and Alignment*, ser. *Curr Top Comp Mol Biol*. Cambridge, Mass.: The MIT Press, 2002) for DNA would be:

MATCH_BONUS: 10
MISMATCH_PEN: −20
INSERTION_PEN: −40
OPENING_PEN: −10
DELETION_PEN: −5

The relationship between the gap penalties (INSERTION_PEN, OPENING_PEN) above help limit the number of gap openings, i.e., favor grouping gaps together, by setting the gap insertion penalty higher than the gap opening cost. Of course, alternative relationships between MISMATCH_PEN, MATCH_BONUS, INSERTION_PEN, OPENING_PEN and DELETION_PEN are possible.

In some embodiments, the methods and systems of the invention incorporate multi-dimensional alignment algorithms. Multi-dimensional algorithms of the invention provide for a "look-back" type analysis of sequence information (as in Smith-Waterman), wherein the look back is conducted through a multi-dimensional space that includes multiple pathways and multiple nodes. The multi-dimensional algorithm can be used to align sequence reads against the DAG-type reference. That alignment algorithm identifies the maximum value for $C_{i,j}$ by identifying the maximum score with respect to each sequence contained at a position on the DAG (e.g., the reference sequence construct). In fact, by looking "backwards" at the preceding positions, it is possible to identify the optimum alignment across a plurality of possible paths.

The modified Smith-Waterman alignment described here, aka the multi-dimensional alignment, provides exceptional speed when performed in a genomic DAG system that employs physical memory addressing (e.g., through the use of native pointers or index free adjacency as discussed above). The combination of multi-dimensional alignment to a reference genomic DAG with the use of spatial memory addresses (e.g., native pointers or index-free adjacency) to retrieve data from objects in the reference genomic DAG improves what the computer system is capable of, facilitating whole genomic scale analysis and read assembly to be performed using the known alleles described herein.

The algorithm of the invention is carried out on a read (a.k.a. "string") and a directed acyclic graph (DAG), discussed above. For the purpose of defining the algorithm, let S be the string being aligned, and let D be the directed acyclic graph to which S is being aligned. The elements of the string, S, are bracketed with indices beginning at 1. Thus, if S is the string ATCGAA, S[1]=A, S[4]=G, etc.

In certain embodiments, for the DAG, each letter of the sequence of a node will be represented as a separate element, d. A predecessor of d is defined as:

(i) If d is not the first letter of the sequence of its node, the letter preceding d in its node is its (only) predecessor;

(ii) If d is the first letter of the sequence of its node, the last letter of the sequence of any node (e.g., all exons upstream in the genome) that is a parent of d's node is a predecessor of d.

The set of all predecessors is, in turn, represented as P[d].

In order to find the "best" alignment, the algorithm seeks the value of M[j,d], the score of the optimal alignment of the first j elements of S with the portion of the DAG preceding (and including) d. This step is similar to finding $H_{i,j}$ in equation 1 above. Specifically, determining M[j,d] involves finding the maximum of a, i, e, and 0, as defined below:

$$M[j,d]=\max\{a,i,e,0\} \quad (6)$$

where $e=\max\{M[j,p^*]+\text{DELETE\_PEN}\}$ for $p^*$ in $P[d]$ $i=M[j-1,d]+\text{INSERT\_PEN}$ $a=\max\{M[j-1,p^*]+\text{MATCH\_SCORE}\}$ for $p^*$ in $P[d]$, if $S[j]=d$;

$\max\{M[j-1,p^*]+\text{MISMATCH\_PEN}\}$ for $p^*$ in $P[d]$, if $S[j]\neq d$

As described above, e is the highest of the alignments of the first/characters of S with the portions of the DAG up to, but not including, d, plus an additional DELETE_PEN. Accordingly, if d is not the first letter of the sequence of the node, then there is only one predecessor, p, and the alignment score of the first/characters of S with the DAG (up-to-and-including p) is equivalent to M[j,p]+DELETE_PEN. In the instance where d is the first letter of the sequence of its node, there can be multiple possible predecessors, and because the DELETE_PEN is constant, maximizing [M[j,p*]+DELETE_PEN] is the same as choosing the predecessor with the highest alignment score with the first j characters of S.

In equation (6), i is the alignment of the first j−1 characters of the string S with the DAG up-to-and-including d, plus an INSERT_PEN, which is similar to the definition of the insertion argument in SW (see equation 1).

Additionally, a is the highest of the alignments of the first j characters of S with the portions of the DAG up to, but not including d, plus either a MATCH_SCORE (if the jth character of S is the same as the character d) or a MISMATCH_PEN (if the jth character of S is not the same as the character d). As with e, this means that if d is not the first letter of the sequence of its node, then there is only one predecessor, i.e., p. That means a is the alignment score of the first j−1 characters of S with the DAG (up-to-and-including p), i.e., M[j−1,p], with either a MISMATCH_PEN or MATCH_SCORE added, depending upon whether d and the jth character of S match. In the instance where d is the first letter of the sequence of its node, there can be multiple possible predecessors. In this case, maximizing {M[j,p*]+MISMATCH_PEN or MATCH_SCORE} is the same as choosing the predecessor with the highest alignment score with the first j−1 characters of S (i.e., the highest of the candidate M[j−1,p*] arguments) and adding either a MISMATCH_PEN or a MATCH_SCORE depending on whether d and the jth character of S match.

Again, as in the SW algorithm, the penalties, e.g., DELETE_PEN, INSERT_PEN, MATCH_SCORE and MISMATCH_PEN, can be adjusted to encourage alignment with fewer gaps, etc.

As described in the equations above, the algorithm finds the optimal (i.e., maximum) value for each read by calculating not only the insertion, deletion, and match scores for that element, but looking backward (against the direction of the DAG) to any prior nodes on the DAG to find a maximum score. Thus, the algorithm is able to traverse the different paths through the DAG, which contain the known mutations. Because the graphs are directed, the backtracks, which move against the direction of the graph, follow the preferred isoform toward the origin of the graph, and the optimal alignment score identifies the most likely alignment within a high degree of certainty.

FIG. 15 describes mapping a sequence read to a DAG 501 and aids in illustrating aligning a sequence to a DAG. In the top portion of FIG. 15, a hypothetical sequence read "ATC-GAA" is presented along with the following two hypothetical sequences:

TTGGATATGGG (SEQ ID NO. 14)

TTGGATCGAATTATGGG (SEQ ID NO. 15)

The middle portion of FIG. 15 is drawn to illustrate that SEQ ID NOS. 14 and 15 relate by a six character indel, where it is pretended that there is a prior knowledge that the hypothetical read aligns to SEQ ID NO. 15, extending into the indel. In the middle portion of FIG. 15, the depiction is linearized and simplified to aid in visualization.

The bottom portion of FIG. 15 illustrates creation of a DAG 501 to which the hypothetical sequence read is aligned. In the depicted DAG 501, SEQ ID NOS. 14 and 15 can both be read by reading from the 5' end of DAG 501 to the 3' end of the DAG, albeit along different paths. The sequence read is shown as aligning to the upper path as depicted.

Figure 16:
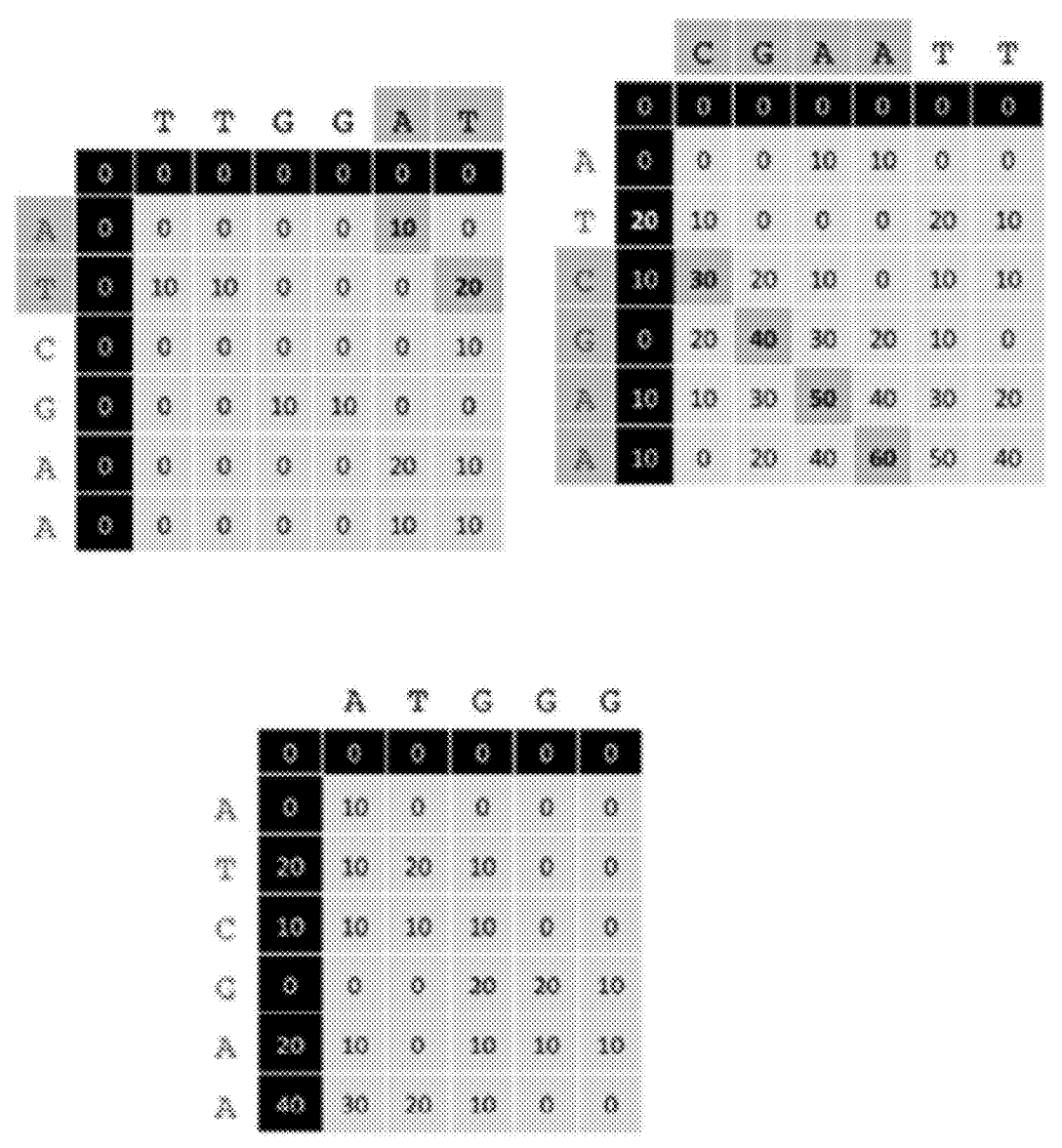

FIG. 16 shows the matrices that represent the comparison. Like the Smith-Waterman technique, the illustrated algorithm of the invention identifies the highest score and performs a backtrack to identify the proper location of the read. In the instances where the sequence reads include variants that were not included in the DAG, the aligned sequence will be reported out with a gap, insertion, etc.

Figure 17:
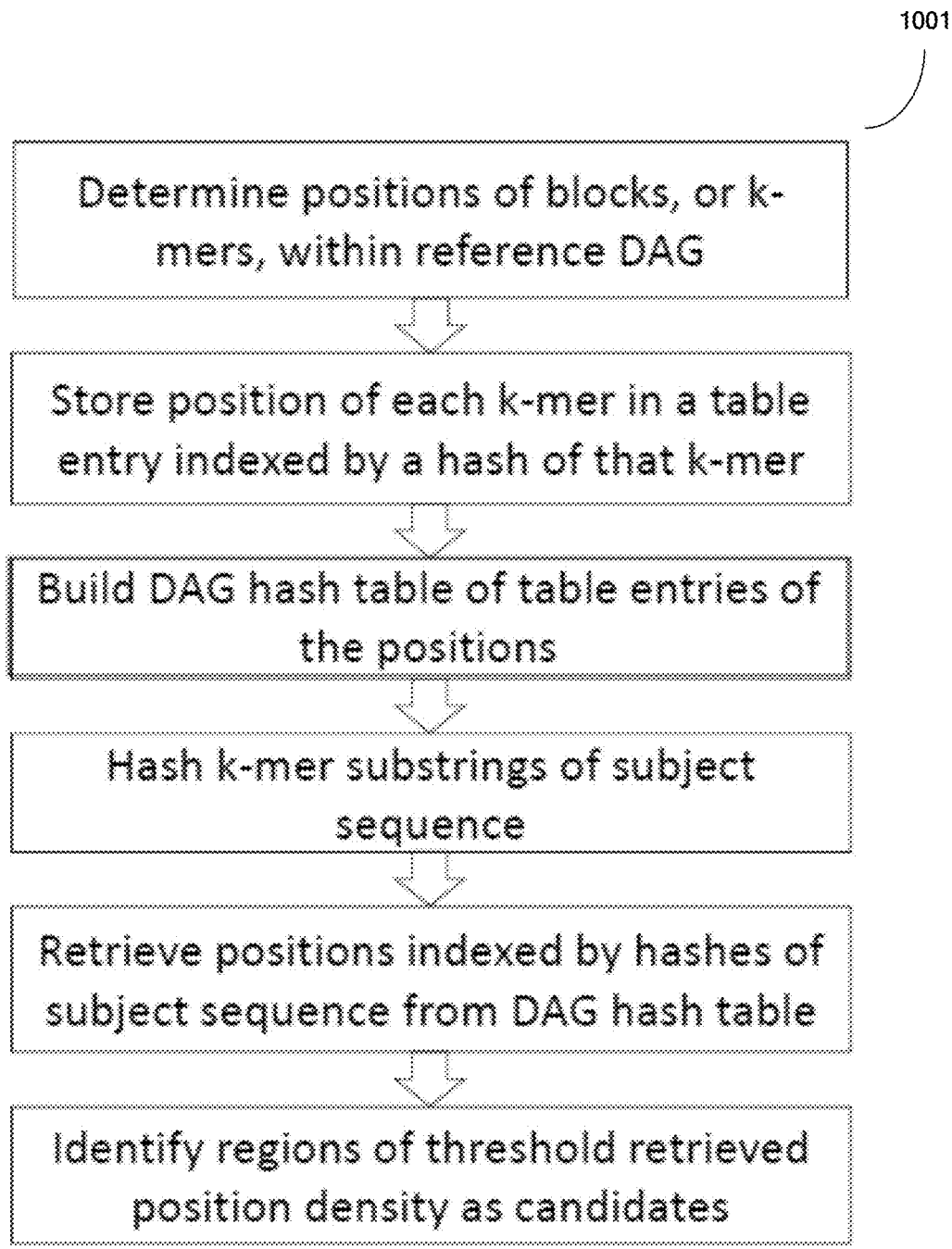
FIG. 17 diagrams a method of the invention.

FIG. 17 gives a diagram of a method 1001 according to certain embodiments. In general, the invention provides a method for analyzing a genetic sequence. The method includes determining positions of k-mers within a DAG that represents a plurality of genomes, storing the positions of each k-mer in a table entry indexed by a hash of that k-mer, and identifying a region within one of the plurality of genomes that includes a threshold number of the k-mers by reading from the table entries indexed by hashes of substrings of a subject sequence. The subject sequence may be mapped to the region within the one of the genomes. The described methods may be performed using software created in any suitable development environment or language.

Any development environment or language known in the art may be used to implement embodiments of the invention. Exemplary languages, systems, and development environments include Perl, C++, Python, Ruby on Rails, JAVA, Groovy, Grails, Visual Basic .NET. An overview of resources useful in the invention is presented in Barnes (Ed.), Bioinformatics for Geneticists: A Bioinformatics Primer for the Analysis of Genetic Data, Wiley, Chichester, West Sussex, England (2007) and Dudley and Butte, A quick guide for developing effective bioinformatics programming skills, PLoS Comput Biol 5(12):e1000589 (2009).

In some embodiments, methods are implemented by a computer application developed in Perl (e.g., optionally using BioPerl). See Tisdall, Mastering Perl for Bioinformatics, O'Reilly & Associates, Inc., Sebastopol, C A 2003. In some embodiments, applications are developed using BioPerl, a collection of Perl modules that allows for object-oriented development of bioinformatics applications. BioPerl is available for download from the website of the Comprehensive Perl Archive Network (CPAN). See also Dwyer, Genomic Perl, Cambridge University Press (2003) and Zak, CGI/Perl, 1st Edition, Thomson Learning (2002).

In certain embodiments, applications are developed using Java and optionally the BioJava collection of objects, developed at EBI/Sanger in 1998 by Matthew Pocock and Thomas Down. BioJava provides an application programming interface (API) and is discussed in Holland, et al., BioJava: an open-source framework for bioinformatics, Bioinformatics 24(18):2096-2097 (2008). Programming in Java is discussed in Liang, Introduction to Java Programming, Comprehensive (8th Edition), Prentice Hall, Upper Saddle River, N.J. (2011) and in Poo, et al., Object-Oriented Programming and Java, Springer Singapore, Singapore, 322 p. (2008).

Applications can be developed using the Ruby programming language and optionally BioRuby, Ruby on Rails, or a combination thereof. Ruby or BioRuby can be implemented in Linux, Mac OS X, and Windows as well as, with JRuby, on the Java Virtual Machine, and supports object oriented development. See Metz, Practical Object-Oriented Design in Ruby: An Agile Primer, Addison-Wesley (2012) and Goto, et al., BioRuby: bioinformatics software for the Ruby programming language, Bioinformatics 26(20):2617-2619 (2010).

Systems and methods of the invention can be developed using the Groovy programming language and the web development framework Grails. Grails is an open source model-view-controller (MVC) web framework and development platform that provides domain classes that carry application data for display by the view. Grails domain classes can generate the underlying database schema. Grails provides a development platform for applications including web applications, as well as a database and an object relational mapping framework called Grails Object Relational Mapping (GORM). The GORM can map objects to relational databases and represent relationships between those objects. GORM relies on the Hibernate object-relational persistence framework to map complex domain classes to relational database tables. Grails further includes the Jetty web container and server and a web page layout framework (SiteMesh) to create web components. Groovy and Grails are discussed in Judd, et al., Beginning Groovy and Grails, Apress, Berkeley, Calif., 414 p. (2008); Brown, The Definitive Guide to Grails, Apress, Berkeley, Calif., 618 p. (2009).

Methods described herein can be performed using a system that includes hardware as well as software and optionally firmware.

Methods described herein can be performed using a system that includes hardware as well as software and optionally firmware.

Figure 18:
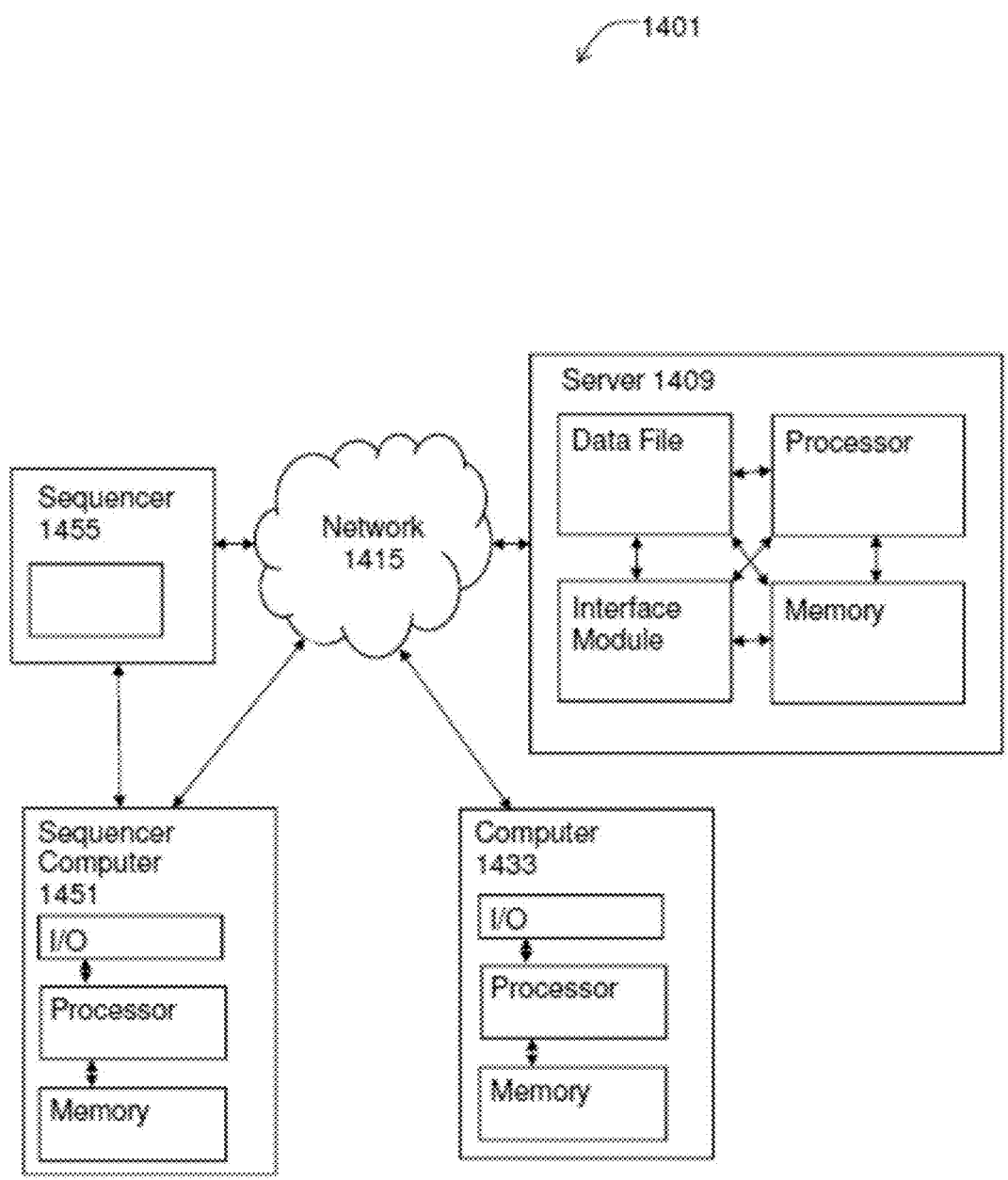
FIG. 18 illustrates a system of the invention.

FIG. 18 illustrates a system 1401 useful for performing methods described herein. Information about identified nucleotides are received at a computer from chip 1405. Sequence reads are received from sequencer 1455, either direct from the instrument or via a computer 1451 used for preliminary collection and any processing of sequence reads. Network 1415 relays data and information among the different computers. Steps of methods described herein may be performed by a server computer 1409 or by a personal computing device 1433 (e.g., a laptop, desktop, tablet, etc.) Computing device 1433 can be used to interact with server 1409 to initiate method steps or obtain results. In generally, a computer includes a processor coupled to memory and at least one input/output device.

A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

Memory generally includes a tangible, non-transitory computer-readable storage device and can include any machine-readable medium or media on or in which is stored instructions (one or more software applications), data, or both. The instructions, when executed, can implement any or all of the functionality described herein. The term "computer-readable storage device" shall be taken to include, without limit, one or more disk drives, tape drives, flash drives, solid stated drives (SSD), memory devices (such as RAM, ROM, EPROM, etc.), optical storage devices, and/or any other non-transitory and tangible storage medium or media.

Input/output devices according to the invention may include a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for analyzing a genetic sequence, the method comprising:

obtaining a reference graph representing a genomic sequence and known variation in the genomic sequence, in which substrings of the genomic sequence and known variation are stored in objects connected to one another to form a plurality of paths through the graph, wherein at least one path through the graph represents substantially an entire chromosome;

identifying a data string for each path of the plurality of paths through the graph, each data string representing a concatenation of the substrings of genomic sequence and known variation in the genomic sequence stored in objects through the path;

for each data string:
identifying a plurality of k-mers in the data string; and
listing each identified k-mer's location within the graph in an entry in a search index, wherein that entry is indexed according to a hash of that k-mer and contains locations of all k-mers having that index;

obtaining a query sequence;

identifying a plurality of query k-mers from the query sequence;

determining the locations of at least one query k-mer within the graph by reading search index entries indexed according to hashes of query k-mers; and identifying portions of the graph in which a number of potential matches with different query k-mers is equal to or exceeds a threshold number as candidate targets within the graph for alignment of segments of the query sequence.

2. The method of claim 1, wherein the query sequence is from a subject organism.

3. The method of claim 1, wherein identifying a plurality of query k-mers from the query sequence further comprises identifying a plurality of query k-mers for the reverse complement of the query sequence.

4. The method of claim 1, wherein each entry of the search index comprises an ordered list of locations for that indexed k-mer.

5. The method of claim 1, wherein each k-mer comprises a sequence of symbols with fixed length k.

6. The method of claim 5, wherein the fixed length k is within an interval [8, 14].

7. The method of claim 1, wherein listing each k-mer's location within the graph further comprises excluding locations identified in a previous path.

8. The method of claim 1, wherein the locations comprise floating point projections for alternate branches.

9. The method of claim 1, wherein sub strings are stored in edge objects connected to one another by vertex objects to form a plurality of paths through the graph.

10. The method of claim 1, further comprising identifying a best-fit location of the query sequence to the graph by performing a local alignment of the query sequence to each candidate target.

11. The method of claim 10, wherein performing a local alignment comprises using a multidimensional Smith-Waterman algorithm.

12. The method of claim 1, wherein the query sequence is a non-contiguous query.

13. The method of claim 12, wherein the non-contiguous query comprises a pair of paired-end sequence reads.

14. The method of claim 13, further comprising identifying portions of the graph in which the number of potential matches with different query k-mers is equal to or exceeds a threshold number within a window of ordered locations.

15. The method of claim 14, wherein the window has a size that is less than 1000 base pairs.

16. The method of claim 1, wherein the chromosome is a human chromosome.

17. A system for analyzing a genetic sequence, the system comprising:

a tangible memory subsystem storing:
a reference graph, the reference graph representing a genomic sequence and known variation in the genomic sequence, in which substrings of the genomic sequence and known variation are stored in objects connected to one another to form a plurality of paths through the reference graph; and a processor executing instructions configured to:
  identify a plurality of paths through the reference graph, each path representing a concatenation of the substrings of the genomic sequence and known variation in the genomic sequence stored in objects through the path;
  for each path of the plurality of paths, identify a plurality of k-mers in the path, and list each identified k-mer's location within the graph in an entry in a search index, wherein that entry is indexed according to a hash of that k-mer and contains an ordered list of locations of all k-mers having that index;
  receive a paired-end sequence read comprising a 5' sequence read and a 3' sequence read; and
  determine candidate targets for alignment of the sequence read by:
    identifying a plurality of query k-mers from the 5' sequence read and the 3' sequence read;
    determining the locations of each query k-mer within the reference graph by reading search index entries indexed according to hashes of query k-mers; and
    identifying portions of the reference graph in which a number of potential matches with different query k-mers is equal to or exceeds a threshold number as candidate targets within the graph for alignment of segments of the sequence read wherein the identifying comprises:
      creating a global ordering of locations corresponding to query k-mers from the 5' sequence read and the 3' sequence read; and
      identifying locations in the global ordering in which both the 5' sequence read and 3' sequence read have query k-mers within a window.

18. The system of claim 17, wherein the window has a size less than 1000 base pairs.

19. A method for analyzing a genetic sequence, the method comprising:
  obtaining a reference graph representing a genomic sequence and known variation in the genomic sequence, in which substrings of the genomic sequence and known variation are stored in objects connected to one another to form a plurality of paths through the graph, wherein at least one path through the graph represents substantially an entire genome;
  identifying a data string for each path of the plurality of paths through the graph, each data string representing a concatenation of the substrings of genomic sequence and known variation in the genomic sequence stored in objects through the path;
  for each data string:
    identifying a plurality of k-mers in the data string; and
    listing each identified k-mer's location within the graph in an entry in a search index, wherein that entry is indexed according to a hash of that k-mer and contains locations of all k-mers having that index;
  obtaining a query sequence;
  identifying a plurality of query k-mers from the query sequence;
  determining the locations of at least one query k-mer within the graph by reading search index entries indexed according to hashes of query k-mers; and
  identifying portions of the graph in which a number of potential matches with different query k-mers is equal to or exceeds a threshold number as candidate targets within the graph for alignment of segments of the query sequence.

20. The method of claim 19, wherein substrings are stored in edge objects connected to one another by vertex objects to form a plurality of paths through the graph.

* * * * *

```
                        SEQUENCE LISTING

<160> NUMBER OF SEQ ID NOS: 15

<210> SEQ ID NO 1
<211> LENGTH: 31
<212> TYPE: DNA
<213> ORGANISM: Homo sapiens

<400> SEQUENCE: 1
ccagaacgtt gcatcgtaga cgagtttcag c                              31

<210> SEQ ID NO 2
<211> LENGTH: 47
<212> TYPE: DNA
<213> ORGANISM: Homo sapiens

<400> SEQUENCE: 2
cccagaacgt tgctatgcaa caagggacat cgtagacgag tttcagc              47

<210> SEQ ID NO 3
<211> LENGTH: 47
<212> TYPE: DNA
<213> ORGANISM: Homo sapiens

<400> SEQUENCE: 3
cccagaacgt tgctatgcag gaagggacat cgtagacgag tttcagc              47

<210> SEQ ID NO 4
<211> LENGTH: 23
<212> TYPE: DNA
<213> ORGANISM: Homo sapiens

<400> SEQUENCE: 4
ttgctatgca ggaagggaca tcg                                        23

<210> SEQ ID NO 5
<211> LENGTH: 12
<212> TYPE: DNA
```

```
<213> ORGANISM: Homo sapiens

<400> SEQUENCE: 5
cccagaacgt tg                                                         12

<210> SEQ ID NO 6
<211> LENGTH: 23
<212> TYPE: DNA
<213> ORGANISM: Homo sapiens

<400> SEQUENCE: 6
catcgtagac gagtttcagc att                                             23

<210> SEQ ID NO 7
<211> LENGTH: 23
<212> TYPE: DNA
<213> ORGANISM: Homo sapiens

<400> SEQUENCE: 7
gacatgagag tccaattctg att                                             23

<210> SEQ ID NO 8
<211> LENGTH: 23
<212> TYPE: DNA
<213> ORGANISM: Homo sapiens

<400> SEQUENCE: 8
gacatgagat tccaattctg att                                             23

<210> SEQ ID NO 9
<211> LENGTH: 27
<212> TYPE: DNA
<213> ORGANISM: Homo sapiens

<400> SEQUENCE: 9
gacatgagag tccacatgat tctgatt                                         27

<210> SEQ ID NO 10
<211> LENGTH: 27
<212> TYPE: DNA
<213> ORGANISM: Homo sapiens

<400> SEQUENCE: 10
gacatgagat tccacatgat tctgatt                                         27

<210> SEQ ID NO 11
<211> LENGTH: 10
<212> TYPE: DNA
<213> ORGANISM: Homo sapiens

<400> SEQUENCE: 11
accgattcga                                                            10

<210> SEQ ID NO 12
<211> LENGTH: 6
<212> TYPE: DNA
<213> ORGANISM: Homo sapiens

<400> SEQUENCE: 12 actcga                                                                 6

<210> SEQ ID NO 13
<211> LENGTH: 10
```

```
<212> TYPE: DNA
<213> ORGANISM: Homo sapiens

<400> SEQUENCE: 13
accgattcga                                                                10

<210> SEQ ID NO 14
<211> LENGTH: 11
<212> TYPE: DNA
<213> ORGANISM: Homo sapiens

<400> SEQUENCE: 14
ttggatatgg g                                                              11

<210> SEQ ID NO 15
<211> LENGTH: 17
<212> TYPE: DNA
<213> ORGANISM: Homo sapiens

<400> SEQUENCE: 15
ttggatcgaa ttatggg                                                        17
```